(12) United States Patent
Dudich et al.

(10) Patent No.: US 8,932,829 B2
(45) Date of Patent: Jan. 13, 2015

(54) RECOMBINANT ALPHA-FETOPROTEIN AND COMPOSITIONS THEREOF

(76) Inventors: Elena Dudich, Moskovskaya Obl. (RU); Lydia Semenkova, Moskovskaya Obl. (RU); Igor Dudich, Moskovskaya Obl. (RU); Eduard Tatulov, Moskow (RU)

( * ) Notice: Subject to any disclaimer, the term of this patent is extended or adjusted under 35 U.S.C. 154(b) by 459 days.

(21) Appl. No.: 12/925,513

(22) Filed: Oct. 22, 2010

(65) Prior Publication Data
US 2011/0159112 A1 Jun. 30, 2011

Related U.S. Application Data

(63) Continuation-in-part of application No. 11/632,409, filed as application No. PCT/RU2005/000369 on Jul. 7, 2005, now Pat. No. 7,910,327.

(51) Int. Cl.
| | |
|---|---|
| *C07K 14/475* | (2006.01) |
| *C12N 1/16* | (2006.01) |
| *C12N 1/19* | (2006.01) |
| *C12N 15/12* | (2006.01) |
| *C12N 15/81* | (2006.01) |
| *C12P 21/02* | (2006.01) |
| *A61K 45/06* | (2006.01) |
| *A61K 33/24* | (2006.01) |
| *A61K 38/17* | (2006.01) |
| *C07K 14/47* | (2006.01) |

(52) U.S. Cl.
CPC . *A61K 45/06* (2013.01); *C12N 1/16* (2013.01); *C12N 15/81* (2013.01); *C12P 21/02* (2013.01); *A61K 33/24* (2013.01); *A61K 38/17* (2013.01); *C07K 14/4715* (2013.01)

USPC ....... 435/69.1; 435/69.6; 435/71.1; 435/71.2; 435/254.2; 530/350; 530/380; 530/395; 530/402

(58) Field of Classification Search
CPC ... A61K 38/18; A61K 38/179; C07K 14/435; C07K 14/47; C07K 14/475; C07K 14/71; C07K 14/4715; C12N 1/16; C12N 1/19; C12N 15/12; C12N 15/81; C12P 21/02
See application file for complete search history.

(56) References Cited

U.S. PATENT DOCUMENTS 6,514,523 B1 * 2/2003 Sparks ..................... 424/450

OTHER PUBLICATIONS

Tecce et al. High-yield and high-degree purification of human alpha-fetoprotein produced by adaptation of the human hepatoma cell line HEP G2 in a serum-free medium. Analytical Biochem 169: 306-311, 1988.*
Tecce et al. Characterization of in vitro expressed human alpha-fetoprotein as highly reproducible reference material for clinical immunoassays. J Nuc Med Allied Sci 34(Suppl 4): 213-216, 1990.*
Mizejewski, GJ. Biological role of alpha-fetoprotein in cancer: prospects for anticancer therapy. Expert Rev Anticancer Ther 2(6): 89-115, 2002.*

(Continued)

*Primary Examiner* — Bridget E Bunner
(74) *Attorney, Agent, or Firm* — Gearhart Law, LLC

(57) ABSTRACT

Disclosed are pharmaceutical and synergistic compositions comprising human recombinant alpha-fetoprotein expressed in eucaryotic cells for preparation of therapeutic agents for use in oncology, immunotherapy, stem cell therapy and cosmetology and also for the diagnosis of cancer and embryonic pathologies.

3 Claims, 28 Drawing Sheets

(56) References Cited

OTHER PUBLICATIONS

Feldman et al. Antitumor activity of alpha-fetoprotein conjugate with doxorubicin in vitro and in vivo. Biochemistry (Moskow) 65(8): 967-971, 2000.*

Lin et al. "Flavoinoids as Neutraceuticals", Chapter 8 in The Science of Flavonoids (2006) USA: Springer Science + Business Media, Inc., pp. 214-238.*

Terrana et al. Clin Chem 36(6): 879-882, 1990.*

Prasad et al. High doses of multiple antioxidant vitamins: essential ingredients in improving the efficacy of standard cancer therapy. J Am Coll Nutr 18(1): 13-25, 1999.*

Mehta et al. Vitamin D and cancer. J Nutr Biochem 13: 252-264, 2002.*

Moskaleva et al. Alpha-fetoprotein mediated targeting-a new strategy to overcome multidrug resistance of tumour cells in vitro. Cell Biol Int. 21(12): 793-799, 1997.*

Severin et al. Alpha-fetoprotein-mediated targeting of anti-cancer drugs to tumor cells in vitro. Biochem Mol Biol Int 37(2): 385-392, 1995.*

Severin et al. Antitumor activity on conjugates of the oncofetal protein alpha-fetoprotein and phthalocyanines in vitro. Biochem Mol Biol Int 43(4): 873-881, 1997.*

Sotnichenko et al. Water-soluble 2,3,7,8-tetrachlorodibenzo-p-dioxin complex with human alppha-fetoprotein: properties, toxicity in vivo and antitumor activity in vitro. FEBS Lett 450: 49-51, 1999.*

Defreest, L.A. et als: "Synthetic peptide derived from alpha—fetoprotein inhibits growth of human breast cancer: investigation of the pharmacophore and synthesis optimization"; I Peptide Res. 2004, 63, pp. 409-419.

Feldman, N. B., et als: "Antitumor Activity of alpha-Fetoprotein Conjugate with Doxorubicin in vitro and in vivo"; Biochemistry (Moscow) vol. 65, No. 8, 2000 pp. 967-971.

Yamamoto, Ritsu, et als: "Expression of Human alpha-Fetoprotein in Yeast"; Life Sciences, vol. 46, No. 23, 1990, pp. 1679-1686 (Pergamon Press).

Smith, Robert, et als: "Heterologous Protein Secretion from Yeast"; Science, vol. 229, pp. 1219-1224 (Sep. 20, 1985).

* cited by examiner

```
1         11         21         31         41         51         61
aagctttagcctaaaaaaaacctctcttgaacttcagtaatacgcttaactgctcat
^HindIII
61        71         81         91        102        111        121
tgctatattgaagtacggattagaaagccgccgagcgggtgacagccctccgaaggaagac
                                        ^BsrBI
121       131        141        151       161        171        181
tctcctccgtgcgtcctcgtcttcaccggtcgcgttcctgaaacgcagatgtgcctcgcg
181       191        201        211       221        231        241
ccgcactgctccgaacaataaagattctacaatactagcttttatggtttatgaagaggaa
241       251        261        271       281        291        301
aaattggcagtaacctggccccacaaaccttcaaaatgaacgaatcaaattaacaaccata
301       311        321        331       341        351        361
ggatgataaatgcgattagtttttttagccttatttctgggtaattaatcaggcgaagcgat
                                                     ^VspI
361       371        381        391       401        411        421
gattttgatctattaacagatatataaatgcaaaaactgcataaccactttaactaata
   ^Sau3A
421       431        441        451       461        471        481
ctttcaacattttcggtttgtattacttcttattcaaaatgtaataaaagtatcaacaaaa
```

FIG.2a

```
481         491         501         511         521         531         541
aattgttaata tacctctata cgtcaaggag aaaaactacc atgagattcca          4
                                                  M  R  F  P
                                                       ^BsaBI
541         551         561         571         581         591         601
    S  I  F  T  A  V  L  F  A  A  S  A  L  A  A  P  V  N  T          24
tctatcttca ctgcagtttt attcgcagca tcctccgcat tagctgctcc agtcaacact
           ^PstI
601         611         621         631         641         651         661
    T  T  E  D  R  T  A  Q  I  P  A  E  A  V  I  G  Y  L  D  L          44
acaacagaga gatgaaacgg cacaaattcc ggctgaagct gtcatcggtt acttagattta
661         671         681         691         701         711         721
    E  G  D  F  D  V  A  V  L  P  F  S  N  S  T  N  G  L  L          64
gaaggggatt tcgatgttgc tgtttgccat ttccaaacag cacaaataac ggggttattg
721         731         741         751         761         771         781
    F  I  N  T  T  I  A  S  I  A  K  E  E  G  V  S  M  A  K          84
tttataaata ctactattgc cagcattgct gctaaagaag aaggggtatc catggctaaa
                                                             ^NcoI
781         791         801         811         821         831         841
    R  T  L  H  R  N  E  Y  G  I  A  S  I  L  D  S  Y  Q  C  T          104
aggacactgc atagaaatga atagcttcca tattggattc ttaccaatgt act
                                                         ^PstI FIG. 2b
```

```
841       851       861       871       881       891       901
 A  E  I  S  L  A  D  L  A  T  I  E  F  A  Q  F  V  Q  E  A            124
gcagagataagttagtgactggctaccatattttgcccagttgtcaagaagcc 901       911       921       931       941       951       961
 T  Y  K  E  V  S  K  M  V  K  D  A  L  T  A  I  E  K  P  T            144
acttacaaggaagtaagcaaaatggtgaaagatgcattgactgcaattgagaaacccact
                                ^AvaIII        ^MfeI 961       971       981       991       1001      1011      1021
 G  D  E  Q  S  S  G  C  L  E  N  Q  L  P  A  F  L  E  E  L            164
ggagatgaacagtcttcaggtgtgtttagaaaaccagctacctgcctttctggaagaactt 1021      1031      1041      1051      1061      1071      1081
 C  H  E  K  E  I  L  E  K  Y  G  H  S  D  C  C  S  Q  S  E            184
tgccatgagaaagaaattttggagaagtacggacattcagactgctgcagccaaagtgaa
                                                  ^PstI 1081      1091      1101      1111      1121      1131      1141
 E  G  R  H  N  C  F  L  A  H  K  K  P  T  P  A  S  I  P  L            204
gagggaagacataactgttttcttgcacacaaaaagcccactccagcatcgatcccactt
                                                ^ClaI
                                                 .^Sau3A
1141      1151      1161      1171      1181      1191      1201
 F  Q  V  P  E  P  V  T  S  C  E  A  Y  E  E  D  R  E  E  F            224
ttccaagttccagaacctgtcacaagctgtgaagcatatgaagaagacagggagacattc
                                    ^NdeI                ^BspHI
```

FIG.2c

```
1201      1211      1221      1231      1241      1251      1261
 M  N  K  F  I  Y  E  I  A  R  R  H  P  F  L  Y  A  P  T  I      244
atgaacaaattcatttatgagatagcaagaaggcatcccttcctgtatgcacctacaatt 1261      1271      1281      1291      1301      1311      1321
 L  L  W  A  A  R  Y  D  K  I  I  P  S  C  C  K  A  E  N  A      264
cttcttgggctgctcgctatgacaaataattccatcttgctgcaaagctgaaaatgca 1321      1331      1341      1351      1361      1371      1381
 V  E  C  F  Q  T  K  A  A  T  V  T  K  E  L  R  E  S  S  L      284
gttgaatgcttccaaacaaaggcagcaacagttacaaaagaattaagagaaagcagcttg 1381      1391      1401      1411      1421      1431      1441
 L  N  Q  H  A  C  A  V  M  K  N  F  G  T  R  T  F  Q  A  I      304
ttaaatcaacatgcatgtgcagtaatgaaaattttgggaccccgaacttccaagccata
                   ^AvaIII 1441      1451      1461      1471      1481      1491      1501
 T  V  T  K  L  S  Q  K  F  T  K  V  N  F  T  E  I  Q  K  L      324
actgttactaaactgagtcagaagtttaccaaagttaattttactgaaatccagaaacta
                                                      ^SpeI 1501      1511      1521      1531      1541      1551      1561
 V  L  D  V  A  H  V  H  E  H  C  C  R  G  D  V  L  D  C  L      344
gtcctggatgtggcccatgtacatgagcactgttgcagagagatgtgctggattgtctg
                        ^Bsp1407I                    ^PstI
     1571           1581           1591      1601      1611      1621
```

FIG.2d

```
         Q  D  G  E  K  I  M  S  Y  I  C  S  Q  Q  D  T  L  S  N  K      364
      caggatggggggaaaaaatcatgtcctacatatgtcctcaacagacactctgtcaaacaaa
                                      ^NdeI
     1621          1631          1641          1651          1661          1671          1681
       I  T  E  C  C  K  L  T  T  L  E  R  G  Q  C  I  H  A  E             384
      ataacagaatgctgcaaactgaccacgtcgaacgtggtcaatgtataattcatgcagaa
     1681          1691          1701          1711          1721          1731          1741
       N  D  E  K  P  E  G  L  S  P  N  L  N  R  F  L  G  D  R  D         404
      aatgatgaaaaacctgaaggtctatctccaaatctaaacaggttttaggagatagagat
     1741          1751          1761          1771          1781          1791          1801
       F  N  Q  F  S  S  G  E  K  N  I  F  L  A  S  F  V  H  E  Y         424
      tttaaccaattttcttcagggggaaaaaaatatcttctttggcaagttttgttcatgaatat
                                                                  ^BspHI
     1801          1811          1821          1831          1841          1851          1861
       S  R  R  H  P  Q  L  A  V  S  V  I  L  R  V  A  K  G  Y  Q         444
      tcaagagagacatcctcagcttgctgtctcagtaattctaagagttgctaaaggataccag
           ^Bpu10I                                                 ^SspI
     1861          1871          1881          1891          1901          1911          1921
       E  L  E  K  C  F  Q  T  E  N  P  L  E  C  Q  D  K  G  E             464
      gagttattggagaagtgttttccagactgaaaaccctcttgaatgccaagataaaggagaa
     1921          1931          1941          1951          1961          1971          1981
       E  L  Q  K  Y  I  Q  E  S  Q  A  L  A  K  R  S  C  G  L             484
      gaagaattacagaaatacatccaggagagccaagcattggcaaagcgaagcgaagctgcggcctc
```

FIG.2e

```
1981          1991          2001          2011          2021          2031           2041
 F   Q   K   L   G   E   Y   Y   L   Q   N   A   F   L   V   A   Y   T   K   K            504
ttccagaaactaggagaatattacttacaaaatgcgtttctcgttgcttacacaaagaaa
                               ^SspI 2041          2051          2061          2071          2081          2091           2101
 A   P   Q   L   T   S   E   L   M   A   I   T   R   K   M   A   A   T   A            524
gcccccagctgacctcgtcggagctgatggccatcaccagaaaaatggcagccacagca
      ^PvuII                                    ^BsaBI
                                                     ^BalI 2101          2111          2121          2131          2141          2151           2161
 A   T   C   C   Q   L   S   E   D   K   L   L   A   C   G   E   G   A   A   D        544
gccacttgttgccaactcagtgaggacaaactattggcctgtggcgaggagcggctgac
                                                                           ^BsrBI 2161          2171          2181          2191          2201          2211           2221
 I   I   I   G   H   L   C   I   R   H   E   M   T   P   V   N   P   G   V   G        564
attattatcggacacttatgtatcagacatgaaatgactccagtaaacccggtgttggc
                                                                           ^BalI 2221          2231          2241          2251          2261          2271           2281
 Q   C   C   T   S   S   Y   A   N   R   R   P   C   F   S   S   L   V   V   D        584
cagtgctgcacttcttcatatgccaacaggaggccatgcttcagcagcttggtggtggat
                       ^NdeI 2281          2291          2301          2311          2321          2331           2341
 E   T   Y   V   P   P   A   F   S   D   D   K   F   I   F   H   K   D   L   C        604

FIG.2f
```

```
     gaaacatatgtccctcctgcattctctgatgacaagttcattccataaggatctgtgc
           ^NdeI.                         .         ^Sau3A  .
     2341      2351      2361      2371      2381      2391      2401
      Q   A   Q   G   V   A   L   Q   T   M   K   Q   E   F   L   I   N   L   V   K    624
     caagctcagggtgtagcgctgcaaacgatgaagcaagagttctcattaaccttgtgaag
           ^Bpu10I      ^Eco47III
     2401      2411      2421      2431      2441      2451      2461
      Q   K   P   Q   I   T   E   E   Q   L   E   A   V   I   A   D   F   S   G   L    644
     caaaagccacaaataacagaggaacaacttgaggctgtcattgcagatttctcaggcctg
                                                                    ^StuI   .
     2461      2471      2481      2491      2501      2511      2521
      L   E   K   C   C   Q   G   Q   E   Q   E   V   C   F   A   E   E   G   Q   K    664
     ttggagaaatgctgccaaggccaggaacaggaagtctgcttgctgaagagggacaaaaa
     2521      2531      2541      2551
      L   I   S   K   T   R   A   A   L   G   V   &
     ctgattcaaaaactcgtgctgctttggggagtttaa
```

FIG.2g

```
  1                  11                 21                 31                 41                 51                 61
  M  A  K  G  T  L  H  R  N  E  Y  G  I  A  S  I  L  D  S  Y
atggc taaggtacctt gcatagaaat gaatatggta ttgcttctat ttttgattct tat
     ^NcoI    ^KpnI                                              ^BsaBI
 61                  71                 81                 91                101                111                121
  Q  C  T  A  E  I  S  L  A  D  L  A  T  I  F  F  A  Q  F  V
caatgtactg ctgaaatttc tttggctgat ctggctacta tttttttgct caatttgtt
121                 131                141                151                161                171                181
  Q  E  A  T  Y  K  E  V  S  K  M  V  K  D  A  L  T  A  I  E
caagaagcta cttataaaga agtttctaaa atgttaaaga tgctttgact gctattgaa
181                 191                201                211                221                231                241
  K  P  T  G  D  E  Q  S  G  C  L  E  N  Q  L  P  A  F  L
aaaccaactg gtgatgaaca atctggtggt tgtttggaaa atcaattgcc agcttttttg
                                                             ^MfeI
241                 251                261                271                281                291                301
  E  E  L  C  H  E  K  E  I  L  E  K  Y  G  H  S  D  C  C  S
gaagaattgt gtcatgaaaa agaaatttt ggaaaaatat ggtcattctg attgttgttct
      ^BspHI
301                 311                321                331                341                351                361
  Q  S  E  E  G  R  H  N  C  F  L  A  H  K  R  P  T  P  A  S
caatctgaag aaggtagaca taattgtttt tgctcataaa aaaccaactc cagcttct
```

FIG. 3A

```
361         371         381         391         401         411         421
 I  P  L  F  Q  V  P  E  P  V  T  S  C  E  A  V  E  E  D  R             140
attccattgttcaagttccagaaccagttacatcttgtgaagcatatgaagaagataga
                                              ^NdeI
421         431         441         451         461         471         481
 E  T  F  M  N  K  F  I  Y  E  I  A  R  R  H  P  F  L  Y  A             160
taaggtaacaaagttcaagtcttgtcaatgtctagagacactcgtatacttcttctatct
gaaacttttgttatgaataaatttattatgaaattgctagagacatcattttgtatgct
cttacgatctctctgtaggtaaaacatacga 491         501         511         521         531         541
 P  T  I  L  L  W  A  A  R  Y  D  K  I  P  S  C  C  K  A               180
ccaactatttgtgggctgctagatatgataaaattattcatctcttgtgtaaagct
ggttgataaacaacccgacgatctatactatttaataaggtagaacacatttcga 541         551         561         571         581         591         601
 E  N  A  V  E  C  F  Q  T  K  A  A  T  V  T  K  E  L  R  E            200
gaaaatgctgttgaatgttttcaaactaaagctgctactgttactaagaattgagagaa
cttttacgacaacttacaaagtttgattcgacgatgactaactagttcttaactctctt 601         611         621         631         641         651         661
 S  S  L  N  Q  H  A  C  A  V  M  K  N  F  G  T  R  T  F               220
tcttcttgttgaatcaacacgcatgcgcgttatgaaaaattttggtactagaactttt
```

FIG.3b

```
     agaagaaacaacttagtgttgtgcgtacgcgacaatactttaaaaccatgatcttgaaaa
661    .    671       .    681       .    691       .    701       .    711       .    721
      Q   A   I   T   V   T   K   L   S   Q   K   F   T   K   V   N   F   T   H   I     240
                           ^SphI
     caagctattactgttactaaattgtctcaaaaatttactaagttaattttactgaatt
     gttcgataatgacaatgattaacagagttttaaatgattcaattaaaatgactttaa
721    .    731       .    741       .    751       .    761       .    771       .    781
      Q   K   L   V   L   D   V   A   H   V   H   E   H   C   C   R   G   D   V   L     260
     caaaaattggtttgatgttgtctcatgttcatgaacattgttgtagaggtgatgtttg
     gtttttaaccaaaactacaacgagtacaagtacttgtaacacatcccactacaaaac
781    .    791       .    801       .    811       .    821       .    831       .    841
      D   C   L   Q   D   G   E   K   I   M   S   Y   I   C   S   Q   Q   D   T   L     280
                                            ^BspHI
     gattgttgcaagatggtgaaaaattatgtcttatatgtcttcaacaagatacttg
     ctaacaacgttctaccacttttaatacagaataataaacagagttgttctatgaaac
841    .    851       .    861       .    871       .    881       .    891       .    901
      S   N   K   I   T   E   C   C   K   L   T   T   L   E   R   G   Q   C   I   I     300
     tctaataaaattactgaatgttgtaaattgactacttggaaagaggtcaatgcattatt
     agattatttaatgacttacaacattaactgatgaaacctttctccagttacgtaataa
901    .    911       .    921       .    931       .    941       .    951       .    961
      H   A   E   N   D   K   P   E   G   L   S   P   N   L   N   R   F   L   G         320
                                                             ^AvaIII
     catgctgaaaatgatgaaaaccagaaggtttgtctccaaatttgaatagatttttgggt
     gtacgactttactacttttggtctttttcaaacagagttaaacttatctaaaaaccca
```

FIG.3c

```
961         971         981         991        1001        1011        1021
  D   R   D   F   N   Q   F   S   G   E   K   N   I   F   L   A   S   F   V        340
gatagagatttaatcaattctcttctgtgaaaaaatatttttggctctctttgtt
ctatctctaaaattagtaaagagaacactcttttaaaaaacgaagaaaacaa
         ^BsaBI                              ^SspI              ^BspHI 1021        1031        1041        1051        1061        1071        1081
  H   E   Y   S   R   R   H   P   Q   L   A   V   S   V   I   L   R   V   A   K    360
catgaatatctagagacatccacaattagctgttctgttctgttatttgagagttgctaaa
gtacttataagatctctgtaggtgttaatcgacaaagacaataaaactctcaacgattt
    ^SspI   ^XbaI 1081        1091        1101        1111        1121        1131        1141
  G   Y   Q   E   L   E   K   C   F   Q   T   E   N   P   L   E   C   Q   D        380
ggttatcaagaattgttgaaaaatgtttcaaactgaaactccattggaatgtcaagat
ccaatagtcttaacaacttttacaaagttgacttttagtgacttacagttcta 1141        1151        1161        1171        1181        1191        1201
  K   G   E   E   L   Q   K   Y   I   Q   E   S   Q   A   L   A   K   R   S        400
aaaggtgaagaagaattgcaaaaatacattcaagaatctcaagcattggctaaaagatcc
tttccacttcttcttaacgttttatatataagttcttagagttcgtaaccgatttctaga
                                                    ^BglII
                                                         ^Sau3A 1201        1211        1221        1231        1241        1251        1261
  C   G   L   F   Q   K   L   G   E   Y   Y   L   Q   N   A   F   L   V   A   Y    420
tgtggtttgttcaaaaattgggtgaatattttgcaaaatgcttttttggttgcttat
acaccaaacaagttttaacccacttatataaacgttttacgaaaaacaacgaata
```

FIG. 3D

```
                                      ^SspI
      1261        1271        1281        1291        1301        1311        1321
       T   K   K   A   P   Q   L   T   S   S   E   L   M   A   I   T   R   K   M   A      440
      actaaaaagctccacattaacttctctgaattgatggctattactagaaaatggct
      tgattttttcgaggtgttaattgaagactaactaccgataatgatcttttaccga 1322        1331        1341        1351        1361        1371        1381
       A   T   A   A   T   C   C   Q   L   S   E   D   K   L   L   A   C   G   E   G      460
      gctactgctgctacttgtgtcaattatctgaagataaattgttggcttgtggtgaaggt
      cgatgacgacgatgaacacagttaatagacttctatttaacaaccgaacaccacttcca 1381        1391        1401        1411        1421        1431        1441
       A   A   D   I   I   G   H   L   C   I   R   H   E   M   T   P   V   N   P         480
      gctgctgatatcattattggtcattgtattagacatgaaatgactccagttaatcca
      cgacgactatagtaataaccagtaacatatctgtacttactgaggtcaattaggt
              ^EcoRV 1441        1451        1461        1471        1481        1491        1501
       G   V   G   Q   C   C   T   S   Y   A   N   R   R   P   C   F   S   S   L          500
      ggtgttggtcaatgttgtacttcttcttatgctaatagagaccatgttttcttttg
      ccacaaccagttacaacatgaagaataccgattatctcttggtacaaaagaagaaac 1501        1511        1521        1531        1541        1551        1561
       V   D   E   T   Y   V   P   P   A   F   S   D   D   K   F   I   F   K             520
      gttgttgatgaaactatgttccaccagttccaccagcttttctgatgataattatttcataaa
      caacaactacttgaatacaaggtggtcgaaaagactactattaaataaaagtattt
```

FIG.3e

```
1561       1571       1581       1591       1601       1611       1621
  D    L    C    Q    A    Q    G    V    A    L    Q    T    M    K    Q    E    F    L    I    N    540
gatttgtgtcaagctcaaggtgttgtgcttgcaaacatgaacaagaatttcttgattaat
ctaaacacagttcgagttccacacgaacgtttgtatacttgttccttaagaactaatta
                                            ^EcoRI    ^VspI.

1621       1631       1641       1651       1661       1671       1681
  L    V    K    Q    K    P    Q    I    T    E    Q    L    E    A    V    I    A    D    F    560
ttggttaaacaaaaaccacaaattactgaagaacaattagaggctgttattgctgatttt
aaccaatttgttttggtgtttaatgacttcttgttaatctccgacaataacgactaaaa 1681       1691       1701       1711       1721       1731       1741
  S    G    L    E    K    C    C    Q    G    Q    E    Q    E    V    C    F    A    E    E    580
tctggtttgttggaaaatgttgtcaaggtcaagaacaagaagtttgttgctgaagaa
agaccaaacaacctttacaacagttccagtcttgttctttcttcaaacaaaacgactctt 1741       1751       1761       1771       1781       1791
  G    Q    K    L    I    S    K    T    R    A    A    L    G    V    &    L    E         597
ggtcaaaaattgatttctaaaactagagctgctttgggtgttaactcgagatat
ccagttttaactaaagattttgatctcgacgaaaccacaaattgagctctata
                                            ^XhoI FIG.3f
```

RECOMBINANT ALPHA-FETOPROTEIN AND COMPOSITIONS THEREOF

PRIORITY

This application claims priority of U.S. application Ser. No. 11/632,409 filed on 1/12/2007, now issued as U.S. Pat. No. 7,910,327 which is a national application of PCT/RU2005/000369 filed on 0707/2005.

FIELD OF INVENTION

The invention relates to the microbiological and medical industry, genetic engineering, and biotechnology. A recombinant alpha-fetoprotein (AFP) according to the instant invention, retaining the activity of a human AFP, obtained from serum, is intended for use in oncology, immunotherapy, and cosmetology.

BACKGROUND OF THE INVENTION

Alpha-fetoprotein (AFP) is the main component of embryonic blood serum of mammals, which is synthesized by embryonal liver and yolk sac during perinatal development. Immediately after birth, the level of AFP in the serum sharply decreases and its expression became undetectable in healthy adult individuals (Deutsch H. F., 1992, Adv. Canc. Res. 56, 253-312). The synthesis of AFP is renewed upon malignant development of liver tumors and germinogenic teratoblastomas and could be detectable to a lesser degree in the case of chemical and mechanical damage to the liver, accompanied by regeneration, for example, during acute viral hepatitis or cirrhosis (Mizejewsky G. J., 2002, Expert Rev. Anticancer. Ther. 2: 89-115).

Human AFP is a glycoprotein consisting of 590 amino acids and comprising about 4% of a carbohydrate component (Morinaga T., et al., 1983, Proc. Natl. Acad. Sci., USA, 80, 4604-4608; Pucci P. et al., 1991, Biochemistry 30, 5061-5066). One of the main properties of AFP is the noncovalent sorption of different low-molecular chemical substances, such as polyunsaturated fatty acids, steroidal hormones, metals, retinoids, hydrophobic antibiotics and others (Aussel, S. & Masseyeff, R., 1994, Biochem. Biophys. Res, Commun. 119: 1122-1127; Deutsch H. F., 1994, J. Tumor Marker Oncol., 9:11-14). In early stages of embryonic development, AFP replaces albumin as a transport vehicle for fatty acids and other low-molecular substances (Deutsch H. F, 1991, Adv. Canc. Res. 56, 253-312).

AFP molecule consists of three globular structural domains bounded by 15 interchain disulfide bonds, which significantly increase the complexity of the process of assembly of a tertiary structure of a protein (Morinaga T., et al., 1983, Proc. Natl. Acad. Sci. U.S.A., 80, 4604-4608; Pucci P. et al., 1991, Biochemistry 30, 5061-5066). Furthermore, an important structural element of an AFP molecule is the carbohydrate component, which provides correct reception and functioning of the molecule (Deutsch H. F, 1991, Adv. Canc. Res. 56, 253-312).

In addition to a polypeptide chain consisting of 590 amino acid residues, the structure of the molecule of a serum embryonic AFP or that one secreted by hepatocarcinoma cells includes on oligosaccharide group linked to asparagin according to the N-type glycosylation (Yamasita K. et al., 1993, Cancer Res. 53: 2970-2975). The structure of an oligosaccharide AFP chain is heterogenous and depends on different factors: the stage of development of hepatocarcinoma or the stage of development of the embryo. Oligosaccharides affect structural properties of an AFP molecule, could be included in the content of antigenic determinants and receptor-binding centers (Deutsch H. F, 1991, Adv. Canc. Res. 56, 253-312). As distinctive from serum AFP, recombinant AFP expressed in bacterial cells is not glycosylated, which is a characteristic distinction of the product characterized in the works of Murgita (U.S. Pat. Nos. 6,33,611; 6,627,440; 6,416,734) and, consequently, has structural and functional properties distinguishing it from a serum analog and also from the recombinant AFP expressed in yeast systems. It is known that during expression of heterologic proteins in yeasts, their glycosylation is carried out in respect to the same amino acid residues as in the serum analog, but the structure of the oligosaccharides themselves significantly differ in respect to makeup, length and branching of the chain, which also predetermines certain distinctions in the structural and functional properties of corresponding proteins (Hard K. et al., 1998, FEBS Lett. 248:111).

AFP may be selectively absorbed by cells expressing specific AFP receptors (AFPR), such as embryonic cells, activated immune cells, cancer cells or cells transformed by certain types of retroviruses (Uriel J. et al., 1989, in Jizejewsky G. I., Jacobson H. L. (eds): Biological Properties of Alpha-Fetoprotein. Boca Raton, CRC Press, vol. 2: 103-117). Normal mature cells lose the ability to absorb AFP and do not express specific AFPR. In view of this property of AFP, methods have been proposed for the therapeutic use of AFP for the purpose of targeting delivering of cytostatics and other substances, suppressing he growth of caner cells, to a tumor (Deutsch H F., 1994, J. Tumor Marker Oncol. 9: 11-14; Tsukada Y. et al., 1994, J. Tumor Marker Oncol. 9: 99-103).

AFP has a number of functional properties, which at present are being intensively studied. The classical concept of AFP as an analog of embryonic serum albumin, is at present supplemented by data concerning the capability of AFP to carry out the regulation of the growth, development and programmed death of cells (Mizejewsky, G. J., 2002, Expert Rev. Anticancer. Ther. 2: 89-115). In particular, it was shown that a recombinant AFP, similarly to a serum and cultural analog, is capable of suppressing the growth of estrogen-dependent tumoral and normal tissues (Bennett J. A. et al., 1997, Breast Cancer Res. Treat. 45, 169-179; Bennet J. A. et al., 1998, Clinical Cancer Research, 4, 2877-2884). Recently, it was established that the oncosuppressive activity of AFP is carried out in accordance with the mechanism of triggering apoptosis, wish is characterized by typical morphological changes, the arrest of growth, by cytotoxicity and DNA fragmentation (Semenkova, L. N., 1997, Tumor Biol. 18, 261-274; Dudich e. I., et al. 1998, Tumor Biol. 19, 30-40; Dudich E. I., et al., 1999, Eur, J. Biochem. 266: 1-13; Semenkova L, et al., 2003, Eur, J. Biochem, 70:4388-4399).

Earlier studies showed the capability of AFP to regulate differentiation and activation of immune cells. In particular, AFP is capable to suppress immune cells activated with allo- or autoantigens and to inhibit various cytokine gene expression (Yamashita K., et al., 1993, Cancer Res. 52, 2970-2975; U.S. Pat. No. 5,965,528). On the other hand, AFP induces pronounced stimulation of the growth of immature bone marrow cells, stem cells and embryonic cells (Dudich E. I., et al., 1998, Tumor Biol. 19, 30-40; U.S. Pat. No. 6,627,440).

The properties of AFP, and also increased selectivity of absorption of AFP by cancer cells in vivo (Uriel J., et al., 1989, in Mizejewsky G. I., Jakobson H. I., eds: Biological Properties of Alpha-Fetoprotein. Boca Raton, CRC Press, vol. 2: 103-117), revealed the base for its use in medicine as a therapeutic preparation in the treatment of autoimmune (U.S. Pat. No. 5,965,528) and oncological diseases (U.S. Pat.

No. 6,416,734; Mizejewsky G. J., 2002, Expert Rev. Anticancer. Ther. 2: 89-115). Furthermore, traditionally AFP is used as an oncoembryonic marker for early diagnosis of oncological diseases and pathologies of embryonical development (Deutsch H F., 1991, Adv. Canc. Res. 56, 253-312). However, the use of natural AFP as a drug is technologically impossible because of raw material deficiency.

Traditionally, a source for the obtainment of AFP is the blood serum of pregnant women, funic embryonal serum or ascitic fluid of cancer patients. Obviously, non of these sources are acceptable for the production of a protein substance for medical purpose because, in the first place, there is extremely limited access to the source of raw material and the content of AFP therein is low, and in the second place, there is the ever-growing risk of infection with viruses or prions.

Earlier data were published relating to the expression and purification of recombinant AFP (rAFP) in different microorganisms (Yamamoto R., et al., 1990, Life Sciences, 46:1679-1686; Nishi S. et al., 1998, J. Biochem. 104: 968-972; U.S. Pat. No. 5,206,153; U.S. Pat. No. 6,331,611). Thus, the intracellular production of human rAFP was carried out in Saccharomyces cerevisiae (Yamamoto R., et al., 1990, Life Sciences, 46:1679-1686; U.S. Pat. No. 5,206,153) and Escherichia coli (U.S. Pat. No. 6,331,611; Boismenu R., et al., 1997, Protein Expression and Purification. 10:10-26; Bennet J. A., et al., 1997, Breast Cancer Res. Treat. 45, 169-179). The main drawback of these expression systems is the incapability to secrete heterologic protein and the extremely low level of its production. Furthermore, the obtainment of the desired product from a biomass of recombinant strain-producers required that additional procedures of denaturation and renatruration be carried out, which resulted in a significant reduction of the yield of the product and, as consequence, a substantial increase of its cost. Also, in the case of use of bacterial expression system, the problem of contamination of the product with the lipopolysaccharides of the cell, which have known endotoxic activity, is also important.

The technical solution most similar to the instant invention is the strain-producer of human AFP that is described in the references (Yamamoto R., et al., 1990, Life Sciences, 46: 1679-1686; U.S. Pat. No. 5,206,153). In these sources yeast strain-producer Saccharomyces cervisiae with intracellular production of human AFP is disclosed, the amino acid sequence of which comprises an additional section corresponding to the signal peptide of rat AFP. This invention identifies the product of secretion of a yeast strain, which product has the properties of a mature human AFP and has the original sequence SEQ ID NO: 2, which correspond to the sequence of mature human AFP. This specificity distinguishes the product described in the instant invention over the earlier disclosed (Yamamoto R., et al., 1990, Life Sciences, 46: 1679-1686; U.S. Pat. No. 5,206,153). Furthermore, a drawback of this strain described in the cited references is the absence of mechanism for intracellular assembly and secretion of AFP into a cultural liquid, which significantly raises the cost, makes the process of preparing a purified recombinant ADP in preparative amounts more complex and provides an extremely low level of production of AFP. Furthermore, the authors of the cited work (Yamamoto R., et al., 1990, Life Sciences, 46: 1679-1686; U.S. Pat. No. 5,206,153) obtained a modified recombinant AFP, the sequence of which also comprises signal and linker peptide, which limits the possibility of its medical use because of modification of the structure of the protein, resulting in a change of the immunological specificity and as a result thereof, if an increase of the risk of immunoreactive pathology with intravenous or subcutaneous administration.

In the case of heterological secretion production with yeast cells of proteins, for which the correct folding takes place with the formation of disulfide bonds (among them AFP), of importance is the level of production of yeast disulfidisomerases (Pdi) with cells of a producer (Shusta E. V., et al., 1998, Nat. Biotechnol. 16: 773-777). Furthermore, action synergic with this enzyme is provided by an increased amount of he chaperon-like yeast protein BiP (Robinson A. S. et al. 1996, J. Biol. Chem. 271: 10017-10022).

In spite of the fact that yeasts are traditionally considered to be organisms free of secreted proteinases (Chung B. H. & Park K. S., 1998, Biotechnol. Bioeng. 57:245-249), for a number of proteins, including—for HSA, their degradation in the course of culturing yeasts is shown, which is related to the presence of still unidentified proteinases associated with the cell (Chung B. H. & Park K. S., 1998, Biotechnol. Bioeng. 57:245-249; Kang H. A., et al., 2000, Appl. to Microbiol. Biotechnol. 53: 575-582). All of the listed factors require that they be taken into account during the creation of a yeast producer of AFP, effectively secreted in a cultural liquid.

Taking the drawbacks of the methods existing at present for the preparation of a recombinant AFP into account, it becomes obvious that there is a need for further improvement of the technology of the systems for expression and secretion of recombinant AFP, in particular the development of new recombinant strains having the capability for higher expression of a heterological protein with the provision for intracellular assembly of a native tertiary structure and subsequent secretion of the desired product into a cultural liquid.

Thus, the requirement for the development of industrially applicable method of preparing AFP, which in respect to is properties would be identical or similar to human serum AFP and thus would make it possible to use it in those fields where human serum AFP is traditionally used, objectively follows from the state of the art.

The achievement of the stated object is possible by the creation of a new strain of microorganism, which could produce in a cultural medium a polypeptide identical or similar to human serum AFP in respect to its properties.

SUMMARY OF THE INVENTION

In order to prepare a recombinant AFP, the properties of which would be identical or similar to the properties of human serum AFP, it was necessary to develop a strain-producer providing for synthesis and production of AFP in a secreted soluble form.

The strain-producer was obtained with the use of genetic engineering methods by transforming a parent strain with a plasmid, which comprised a DNA sequence encoding a protein having the activity of a mature human AFP.

A recombinant secreted AFP produced in a yeast system of expression has properties to identical or similar to the properties of a mature human AFP, which are determined in an immunologic analysis and by its capability to suppress the growth of cells of B-cell lymphoma Raji and other human cellular lines sensitive to apoptogenic action in a culture in vitro. This provides for an identical mechanism of action of the obtained AFP and a mature human serum AFP, obtained by a traditional method and having an amino acid sequence presented as SEQ ID NO: 2. The conditions for carrying out the method of preparing AFP according the instant invention provides for the assembly of a polypeptide with minimum defects as compared with native human AFP.

The proximity of the properties of human recombinant AFP, produced in yeasts, and human serum AFP is provided by the inclusion of an expression cassette, comprising a DNA sequence encoding a mature human AFP, in the composition of the plasmid, in that the process of isolation does not require the denaturation-renaturation step, and at the same time provides for glycosylation of the obtained polypeptide, and also folding of the molecule and formation of disulfide bonds. Recombinant human AFP produced in a secreted form in a yeast system of expression differs from the recombinant analog produced in a proeukaryotic system of expression in that it is glycosylated according to the N-type, while a recombinant bacterial AFP described in patents (Muragita R. A. U.S. Pat. Nos. 6,331,611; 6,627,440; 6,416,734) is not glycosylated. Human recombinant AFP produced in a secreted form in a yeast system of expression differs from the serum analog by the composition and structure of the oligosaccharide chain, which is determined by the yeast strain and composition of the sugars included in the nutrient medium.

In order to obtain a high yield of the secreted protein with the required activity from a host cell, several additional genes were added to the plasmid encoding the AFP gene, the additional genes providing a high level of gene transcription, folding of the protein in the process of secretion and the correct formation of disulfide bonds.

As a result, a pKX plasmid was obtained having the capability of transforming cells for the expression and secretion of AFP.

A eukaryotic producer cell having the capability of secreting recombinant alpha-fetoprotein was obtained with the aid of the aforesaid plasmid.

In a preferable variant a recipient strain *Saccharomyces cerevisisae* YBS723 was used as the initial cell, this strain being transformed by pKX plasmid to obtain a strain producer *Saccharomyces cerevisiae* YBS723/pKX, deposited in the Russian Collection of Industrial Microorganisms (VKPM) under No. Y-3115.

During the cultivation of a transformed strain, AFP is secreted into a medium from which it may be isolated in a pure form with the use of traditional biochemical methods.

An isolated AFP obtained from transformed cells is used in the content of a pharmaceutical composition inhibiting the growth of tumor cells, which comprises the obtained AFP and pharmaceutically acceptable carriers and excipients.

An isolated AFP is used in the makeup of a synergic composition, inhibiting the growth of tumor cells, which comprises the obtained AFP and chemotherapeutic preparation sand pharmaceutically acceptable carriers and excipients.

With use of the isolated AFP, a pharmaceutical composition on the base thereof or comprising its synergistic composition, a method for treating cancer or preventing development has been developed, which presumes the administration to a patient of an effective amount of AFP, pharmaceutical composition or synergic composition.

Since the obtained AFP is similar in respect to the properties to human serum AFP, the obtained AFP is used in a makeup of a synergic composition having an immunosuppressive and immunoregulating action, wherein the composition comprises AFP and cyclosporin C and pharmaceutically acceptable carriers and excipients.

A method for treating autoimmune diseases and correcting the immune status has been developed with use of the isolated AFP or aforesaid synergic composition, the method comprising administering to a patient an effective amount of an AFP or a synergic composition with cyclosporine C.

In view of the capability of AFP to stimulate growth of stem cells, the inventors have proposed a pharmaceutical composition stimulating the growth of stem cells, the composition comprising the obtained AP and pharmaceutically acceptable carriers and excipients, an a synergic composition stimulating the growth of stem cells is also proposed, this composition comprising the obtained AFP an derivatives of vitamins A, E, D, antioxidants, steroid hormones, isoflavones of vegetative origin with pharmaceutically acceptable carriers and excipients.

A method for stimulating the growth of stem cells in vitro is proposed with use of the isolated AFP, the aforesaid pharmaceutical or synergistic composition, the method comprising acting on cells with an effective amount of AFP or corresponding compositions.

Furthermore, a method for stimulating the growth of stem cells in vivo is proposed, the method comprising administering to a patient an effective amount to AFP or the aforesaid pharmaceutical or synergistic composition.

A cosmetic composition for rejuvenating skin and preventing aging of skin is proposed on the basis of functional activity of isolated AFP. The composition comprising the obtained AFP with carriers and excipients acceptable in cosmetology and, optionally, derivatives of vitamins A, E, D, antioxidants, steroid hormones, isoflavones of vegetative origin.

A method of using the obtained cosmetic composition for rejuvenating the skin and preventing aging of the skin is proposed within the frame of the instant invention, the method comprising applying the composition of to the skin of an individual.

BRIEF DESCRIPTION OF THE DRAWINGS

The following drawings illustrate the present subject matters of the invention.

FIG. 2 A-G shows the structure of an expression cassette comprising a sequence encoding a human alpha-fetoprotein within the compression of a pKX plasmid. The promoter region of the GAL1 yeast gene is shown by italics. The pre-pro region of secretion of the Mfal yeast gene is shown by dark print. The amino acid sequence of the human alpha-fetoprotein molecule (SEQ ID NO: 2) is shown by capital letters.

FIG. 3 A-F demonstrates the structure of a synthetic gene encoding AFP and consisting of the most often used yeast codones. The AFP amino acid sequence of serum human AFP, is singled out with dark print (SEQ ID NO:2).

Figure 1:
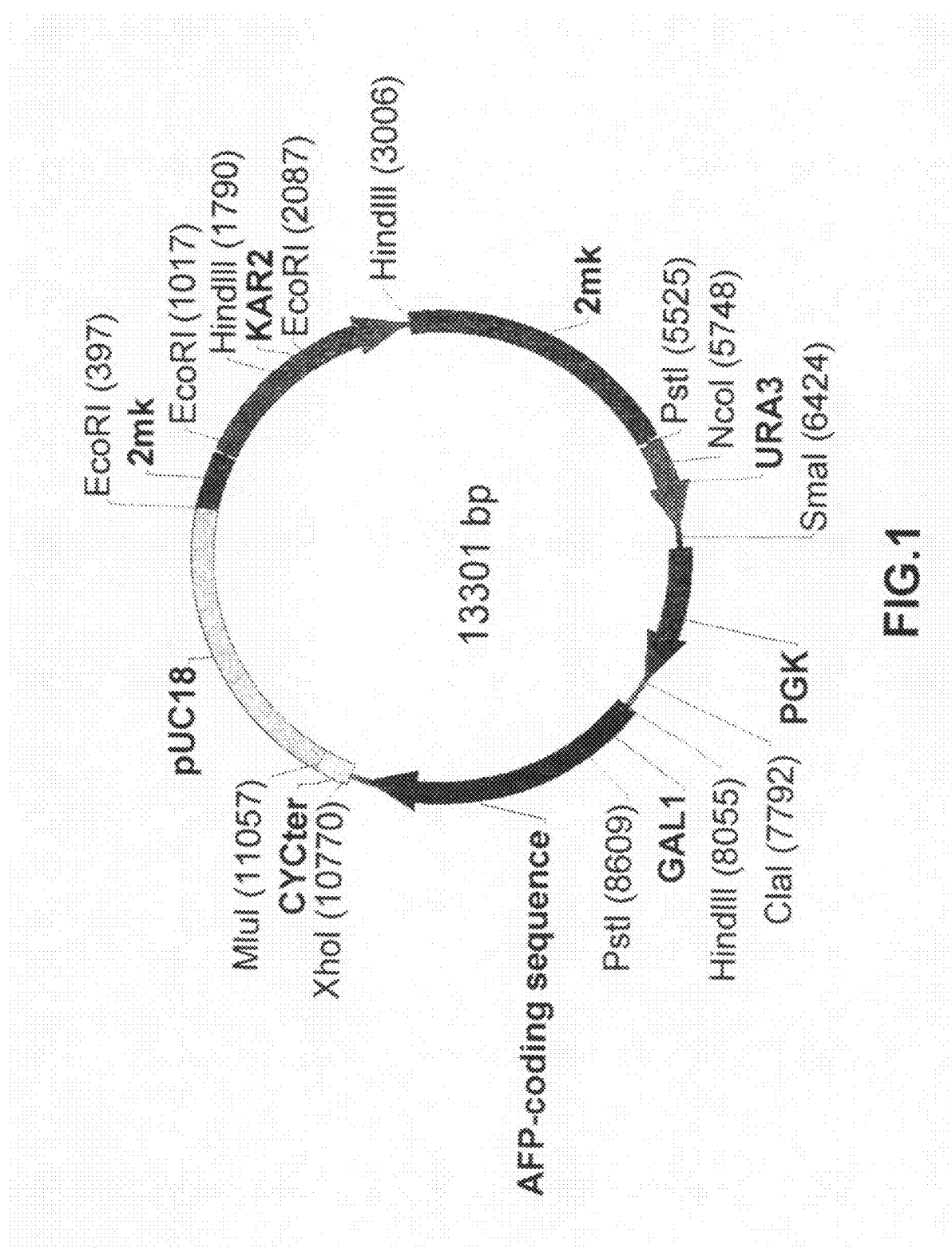
FIG. 1 shows the structure of a pKX plasmid encoding the sequence of a mature human alpha-fetoprotein, comprising an expression cassette with a human alpha-protein gene; a fragment of a bacterial plasmid pUC18; a region of initiation of replication of a 2-μm yeast plasmid; a selective PGK1 yeast marker, a pD11 gene encoding an disulfidisomerase enzyme and a KAR2 gene providing correct assembly of the protein and secretion of the desired product into a culture medium.

The list of sequences comprises sequence SEQ ID NO: 1 and SEQ ID NO: 2, which are respectively the nucleotide sequence of an expression cassette comprising the encoding sequence of human alpha-fetoprotein in the composition of a pKX plasmid and the amino acid sequence of a mature human AFP.

The nucleotide sequence of an expression cassette comprises a promoter region of GAL1 yeast gene, a pre-pro region of secretion of a MFα1 yeast gene, the encoding sequence of a human alpha-fetoprotein gene and a field of termination of transcription of a CYC1 yeast gene. This expression cassette is included in the composition of the pKX plasmid encoding the sequence of a mature human alpha-fetoprotein in a yeast strain-producer of *Saccharomyces cervisiae* YBS723/pKX

DETAILED DESCRIPTION OF THE INVENTION

In order to realize the instant invention, the main technical object was the creation of a strain of yeast-producer of AFP, capable of effectively secreting the desired protein into a cultural liquid. This object is solved by constructing a recombinant DNA pKX plasmid encoding the regulated synthesis of human AFP and the strain *Saccharomyces cerevisiae* YBS723/pKX providing the synthesis and production of AFP in a secreted dissolved form with a level of expression not less than 10 mg/l. The high level of synthesis of the desired protein in secreted dissolved form is provided in that the pKX plasmid comprises a promoter of the GAL1 gene with simultaneous amplification of the KAR2 gene (Robinson A. S., et al. 1996, J. Biol. Chem. 271: 10017-10022), encoding a chaperon heavy chain binding protein BiP. In the genome of the strain of the recipient, there is amplification of the PD11 gene (Robinson A. S., et al., 1996, J. Biol. Chem. 271: 10012-10022), encoding a disulfidisomerase enzyme, which participates in the formation of disulfide bonds during the secretory process of the proteins.

The recombinant plasmid DNA comprises a human AFP gene under the control of a GAL1 promoter gene, providing a high level of transcription of the gene, and a KAR2 gene, encoding a chaperon heavy chain binding protein BiP, participating in folding proteins during the secretory process for the proteins, and providing a high level of production of the desired protein into the cultural liquid, Furthermore, in order to provide the correct formation of disulfide bonds and the formation of a native tertiary structure of the protein, a PS11 gene encoding disulfideisomarase is used.

A recombinant pKX plasmid DNA (FIG. 1), encoding a human AFP gene, is characterized by the following features:
it is an expression plasmid for the effective secretion of human AFP;
it has a size of 13301 bp;
it comprises a fragment encoding the amino acid sequence of a mature human alpha-fetoprotein SEQ ID NO:2;
it comprises a fragment of the bacterial plasmid pUC18; a region of initiation of a 2 µm yeast plasmid; a selective yeast marker PGK1; a KAR2 yeast gene encoding a chaperon heavy chain binding protein BiP; a PD11 gene encoding a disulfisomerase enzyme; an expression cassette with an AFP genome;

in the structure of the expression cassette presented by the nucleotide sequence SEQ ID:NO:1 is included: a promoter region of GAL1 yeast gene; a pre-pro region of secretion of Mfα1 yeast gene; a region encoding a mature human AFP; a field of termination of transcription of a CYC1 yeast gene. When this plasmid is introduced into a cell, a high level of transcription of the AFP gene is achieved due to the use of a highly effective GAL1 promoter. The introduction of a pre-pro region of secretion of Mfα1 provides for the correct secretory processing of AFP accompanied by the effective secretion of the protein with the expected amino acid sequence SEQ ID NO: 2, if the encoding region will correspond to the DNA sequence encoding a mature human AFP in a cultural liquid;

a significant distinction of the proposed plasmid construction is that an AFP gene is under the control of a highly effective GAL1 promoter, and in order to provide the correct formation of disulfide bonds and the formation of a native tertiary structure of the protein, PD11 and KAR2 genes are used.

Any eukaryotic cell susceptible to such a transformation with the indicated plasmid may be transformed with the aid of the created plasmid. The selection to the cell is not critical since the methods and steps of transformation are well known to those skilled in the art. However, depending on the type of cell and the conditions for culturing the obtained transformant, the level of expression of AFP may vary, but the fact of expression of the required peptide will take place under condition of successful transformation of the parent cells.

A recipient strain YBS723 of the genotype pgk1/pgk1 is used to obtain the strain *Saccharomyces cerevisiae* YBS723/pKX. The homozygosis of pgk1/pgk1 makes this strain incapable of growth in all mediums containing any single source of carbon within the norm digestible by yeasts *S. cerevisiae*. The homozygosis of gal80: :PD11/gal80: :PD11 results in a change of regulation of the promoter of the GAL1 gene with simultaneous amplification in the genome of the PD11 gene encoding the disulfidisomerase enzyme and participating in the formation of disulfide bonds during the secretory process of the proteins.

The YBS723 strain is transformed by the pKX plasmid according to the method (Ito H., et al., 1983, J. Bacteriol. 153:163-168). Transformants were selected according to the capability to grow on a full-value yeast medium (bactopeptone—20 g/l, yeast extract—10 g/l, bactoagar—20 g/l) comprising 2% glucose as a source of carbon. One of such clones is designated as YBS723/pKX.

The obtained diploid yeast strain *Saccharomyces cerevisiae* YBS723/pKX is characterized by the following features:
Genetic features: Genotype pgk1/pgk1 gal180: :PD11/gal80: :PD11;
Morphological features: Vegetative cells of a 48-hour culture grown on a solid nutrient medium with 2% sucrose as the only source of carbon have an oval form, cell size of 3.6× 7.1 μm, the protoplasma is homogenous, reproduction is by gemmation. When growing on a solid medium comprising a yeast extract and peptone (YEP) at 30° C. after 72 hours of growth, the columns have the following appearance:
1) on a YEP medium with glucose—a white color column with a smooth edge, shining surface, cone-shaped profile, cream-like consistency;
2) on a YEP medium with starch—a white color column with a pattered edge, dull surface, lens-like profile and grain consistency;
3) on a YEP medium with molasses—a white color column with a dull wrinkled surface, patterned edge, convex profile and cream-like consistency.

Growth on a liquid medium—on YEP medium with starch at 32° C. during the first 24 hours of culturing—a cloudy liquid, white residue, does not cake, does not form parietal films.

Physicochemical features: Facultative anaerobe. Temperatures of growth: 23-33° C. (optimum—31° C.). pH of culturing—3.8-6.7 (optimum—5.0). Highest level of secretion of AFP is observed at pH 6.8-7.0.

Assimilation of carbon sources: ferments glucose, galactose, fructose, maltose, saccharose, dextrine, starch.

Assimilation of nitrogen sources: assimilates amino acids, urea, ammonium, sulphate, ammonium nitrate.

Distinctive specificities: in the case of culturing on a rich medium with starch (2%), zones of fading starch surrounded by a dark rim after incubation of dish at +4° C. for 24 h.

Pathogenicity: the strain *Saccharomyces cerevisiae* YBS723/pKX is not pathogenic.

Method of storage: The strain is stored on an agarized rich medium with glucose for 3 months at +4° C.

The obtained strain *Saccharomyces cerevisiae* YBS723/pKX-producer of AFP in a secreted form is deposited in the Russian Collection of Industrial Microorganisms (VKPM) under NO. Y-3115.

The cell strain producer of recombinant AFP proposed by the Applicants has a number of advantages over already existing prototypes:
production of the desired product is carried out in a secreted form into a cultural liquid.
the amino acid sequence of the final product corresponds to the sequence of a mature human AFP—SEQ ID NO:2;
similar to the serum embryonal analog, rAFP, produced by the strain producer *Saccharomyces cerevisiae* YBS723/pKX, is glycosylated;
the yield of the desired product is significantly increased due to an increase of expression of the gene encoding the disulfidisomearase enzyme PD11 providing for the formation of disulfide bonds and the KAR2 gene encoding chaperon heavy chain binding protein BiP providing for correct assembly of the protein and secretion of the desired product into the cultural medium.

It is clear to one skilled in the art that the sequence encoding the DNA may comprise replacement related to the degeneration of the genetic code, an also some replacements, insertions, deletions, which as a whole do not result in the obtainment of inactive forms of the fetoprotein. Possible variations are known to those skilled in the art. The obtained polypeptide may also include within the frame of the amino acid sequence conservative amino acid replacement presuming the replacement of one amino acid with another having similar properties. However, within the limits of the claimed features of the instant invention there are only those polypeptides which have primary, secondary and tertiary structure, that does not disturb the required activity of obtained polypeptide, in particular—to have properties identical or similar to the properties of a mature human AFP, determined in an immunological analysis and in accordance with its capability to suppress the growth of cells of a B-cellular lymphoma Raji in culture in vitro.

The indexed of functional activity, at which it is regarded that the obtained polypeptide will have the properties of a mature human serum AFP are determined according to the immunological reaction and according to its capability of inhibiting in vitro the growth of cells of the B-cellular lymphoma Raji at a level not less than 10% of the activity of a mature human serumal AFP cells of the B-cellular lymphoma Raji at a level not less than 10% of the activity of a mature human serum AFP.

In the case of practical use of the obtained polypeptide within the makeup of a composition, traditional additional components are used, such as excipients, diluents, preservatives, buffer solutions, physiological solutions, a 0.9% solution of sodium chloride, technological additives used during the production of drug forms, etc. Compositions may be fluid (solutions, suspensions, creams, emulsions, etc.), solid (lyophilized powder, reconstituted prior to use, an absorbed preparation of a carrier etc.), serving for parental, oral, intravenous, intramuscular, etc. administration or for external use. Wherein, the compositions for external use may comprise additives promoting the absorption and diffusion of the active substance in tissue.

The synergic compositions of the instant invention provide for the presence in the compositions of another active substance, wherein in the case where two active substances are present at the same time, on of which is the rhAFP according to the instant invention, the effect of their action is reliably higher than in the case where each substance is used separately.

It is evident that synergic compositions are one of the preferable variants of embodiment of the inventions, since to one skilled in the art the variant of administering each active component separately is clear. For example, in the case of anticancer therapy, each preparation of an active component may be administered separately and together simultaneously, with separation by time or by different manners of administrations. The concrete selection depends on the state of the patient, the seriousness of the illness, prior treatment, etc.

The selection of the therapeutic doses for treatment may be any doses in a wide range from 0.001-10 mg/kg of a patient's weight, with the evidence that the required therapeutic effect is obtained. It corresponds to the traditional dosages of human serum AFP, since the obtained rhAFP will have properties that are similar or close in respect to activity of its serum analogue. The limiting dosages of rhAFP according to the invention correspond to the dosages of human AFP, since they have a similar amino acid sequence, which is not recognized by a normal immune system of human as "foreign".

The instant invention is illustrated by the following examples, which are not of a restrictive character, but are intended to demonstrate embodiment of the invention and realization of the best variant of the embodiment.

EXAMPLE 1

Isolation of Sum RNA and Construction of Intermediate Recombinant Plasmid DNA pTrcafp The total mRNA was isolated from the cellular line of human hepatoma HepG2 with the aid of Trizol Reagent (Gibco BRL, USA) in accordance with a method of the producer. The cDNA was obtained using First Strand cDNA Synthesis Kit (MBI Fermentas) in the presence of primers oligo (dt)$_{18}$ or GAAGTAATTTAAACTCCCAAAGC(3R) (SEQ ID NO:7), complimentary to the 3' end of the gene afp. Amplifications of the obtained matrix for subsequent cloning was carried out in the presence of primers:

```
                                              (SEQ ID NO: 3)
     CTTCAATCGATATGACACTGCATAGAAATG (Cla)

(SEQ ID NO: 4)
     CTTCCAAGCTTAAACTCCCAAAGCAG (Hind),
``` the first of which corresponds to the 5'-sequence of mature protein gene (singled out by dark print) and comprises a recognition site for restrictase Cla I, while the second is complementary to the 3'-end section of the gene (singled out by dark print) and comprises a recognition site for Hind III. Amplification of the gene was carried out in a volume of 100 µl. The reaction mixture compressed 10 ng of cDNA, 30 pM of each of the primers (1) and (2), a mixture of dNTP (0.2 mM of each), 10 mM of Tris-HCL, pH 8.8, 10 mM of KCl, 2.5 mM of MgSO$_4$, 2.5 unit Pfu DNA-polymerases (Stratagene firm) and 1 unit Taq DNA-polymerase (Fermentase firm). There were 25 cycles carried out according to the scheme: 95° C./40 sec, 39° C./40 sec, 72° C./1 min. The products of the reaction were analyzed by electrophoresis in a 1% agarous gel; strips of a length of about 1790 bp were cut, DNA was extracted from the gel, treated with restrictases Cla I and Hind III and cloned into the plasmid pTrcTEGF, earlier obtained with those same restrictases. As a result the plasmid pTrcafp was obtained; its structure was confirmed by restrictase analysis, using restrictase Cla I and Hind III, in respect to which cloning was carried out, and also Spe I, Mun I, Sec I and Sty I, the recognition sites of which are is inside the AFP gen, and by determination of the nucleotide sequence of the DNA section cloned with the aid of PCR. Sequencing was carried out according to the method and with use of the Cycle Reader™ DNA Sequencing Kit (Fermentas, Lithuania).

EXAMPLE 2

Preparation of Synthetic cDNA, Encoding a Human AFP Gene

In order to obtain a synthesized AFP gene, 36 oligonucleotides having a length of 62-68 b were chemically synthesized. On the basis of these oligonucleotides size double-chain fragments were obtained by the method of polymerase chain reaction, each of which was cloned to a vector pUC18. The primary structure of all the cloned fragments was confirmed by sequencing. Fragments with the correct nucleotide structure were then sequentially collected into a desired gene by the method of restriction/ligation in the form of a fragment of the plasmid pUC18. In a similar manner a cDNA was obtained for expression of modified forms of AFP, comprising deletion, mutation or added amino acid residues.

EXAMPLE 3

Construction of a Recombinant Plasmid DNApKX

The plasmid pTrcafp was used as a matrix for PCT in the presence of primers:

```
                                              (SEQ ID NO: 5)
         CAACCCTCGAGTTAAAACTCCCAAAGC (SEQ ID NO: 6)
         CCAACCCATGGCTAAGAGAACACTGCATAGAAA-TG.
```

Restriction sites NcoI and XhoI (underlined) are set in the sequence of primers. The DNA fragment obtained as a result of amplification after treatment with endonucleasase of restriction NcoI/XhoI were cloned onto vector pUC18/GAL1-pp, comprising a promoter GAL1 and pre-pro region of secretion MFα1. As a result the plasmid pUC18/GAL1-ppafp was obtained. In order exclude possible errors of PCR the NcoI/XhoI fragment of the plasmid was sequenced. The HindIII/XhoI fragment of the plasmid pUC18/GAL1-pp/afp, comprising the promoter GAL1, pre-pro region of secretion of MFα1 and encoding part of the human AFP gene (FIG. 2) were transferred to the HindIII/XhoI bireplicon (yeast-*E. coli*) vector pPDX. As a is result the plasmid pPDX/GAL1-pp/afp was obtained. The ClaI/XhoI fragment of the plasmid pPDX/GAL1-pp/afp was transferred to ClaI/XhoI vector of pPK, differing from pPDX by the presence of the KAR2 gene. The plasmid obtained as a result is named pKX (FIG. 1). In a similar manner the plasmid pKX-1 was obtained, comprising the synthetic human AFP gene consisting of the most widely used yeast codons (FIG. 3). The plasmid pKX-1 differs from pKX in that it comprises the synthetic gene of a mature human AFP.

EXAMPLE 4

Obtainment of a Strain-Producer of Human AFP

In order to obtain the strain *Saccharomyces cervisiae* YBS723/pKX, the recipient strain YBS723 was transformed by the plasmid pKX in accordance with the method (Ito H., et al., 1983, J. Bacteriol. 153: 163-168). The transformants were selected by the capability to grow on a full-value yeast medium (bactopepton—20 g/l, yeast extract—10 g/l, bactoagar—20 g/l), comprising 2% glucose as the source of carbon. One of such clones is designated YBS723/pKX.

EXAMPLE 5

Figure 4:
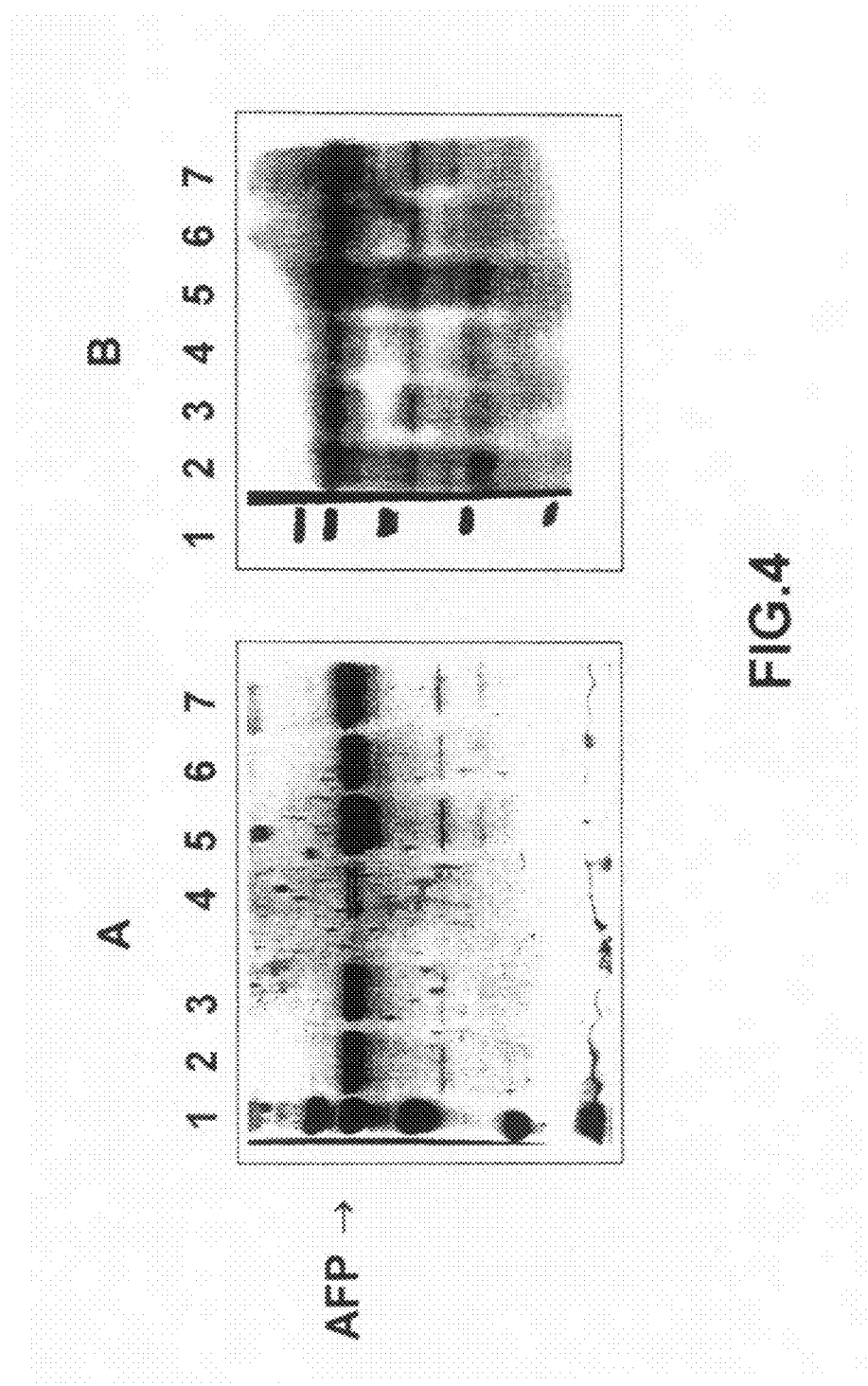
FIG. 4 shows the results of SDS-PAGE electrophoresis (A) and immunoblotting-analysis (B) of different amounts, applied onto a line, of a purified recombinant alpha-fetoprotein obtained from a yeast culture *Saccharomyces cervisiae* YBS723/pKX cultural liquid.
 1. Marker proteins (94, 67, 43, 30, 20 kD).
 2. rAFP after affinity chromatography on a column with anti-AFP-sepharose (0.3 μg)
 3. rAFP after gel-chromatography on a column with Sephacryl S-200 (0.4 μg).
 4. rAFP (0.1 μg).
 5. rAFP after Sephacryl S-200 (0.6 μg).
 6. rAFP after Sephacryl S-200 (0.5 μg)
 7. Embryonic eAFP (0.4 μg).

Determination of Productivity of Strain-Producers of Human AFP *Saccharomyces cerevisiae* YBS723/pKX Cells of the strain-producer YBS723/pKX were grown in vials at 26° C. on a rocker (250 rpm) on a medium of the following composition: glucose—2%, glycerine—1.5%, yeast extract—1%, peptone—2%, distilled water. The pH of the medium was maintained at 7.0 by the addition of 0.1M of a phosphate buffer. The initial titer of the cells was $5 \times 10^6$. Samples were taken after 72 hours of growth of the culture after transition to the stationary phase of growth at a titer of $7-8 \times 10^8$. A sample of the cultural liquid was obtained after centrifugation of the culture at 10 0000 rpm for 1 min and was used in the following analyses. Samples of the CL were analyzed by electrophoresis in a 12.5% polyacrylamide gel with sodium dodecyl sulphate. The gels were colored Coomassie R-250 (FIG. 4) and scanned to determine the total protein and relative content of the AFP specific protein. According to the data of electrophoresis and scanning, the total content of AFP in the CL is about 10-25% of the total protein, but there is partial intracellular degradation of the protein. The relative content of AFP in the CP was determined by the method of immunoblotting in the presence of polyclonal antibodies to AFP (FIG. 4). Also, the quantitative content of AFP in the cultural liquid was determined by the method of immunoenzymatic analysis (IEA), with the use of a set of monoclonal and polyclonal antibodies to human AFP. According to the IEA data, the average content of AFP in the CL in liquid mediums reached 5 mg/ml.

EXAMPLE 6

Determination of Productivity of Strain-Producer of Human AP *Saccharomyces cerevisiae* YBS723/pKX in High-Density Mediums Feed-back culturing the strain YBS723/pKX was carried out in a fermenter at 26° C. and pH 7.0 (automatic maintenance). The content of dissolved oxygen dO was maintained >20%. During fermentation, replenishment with a medium of the following composition was carried out: yeast extract—30 g/l, peptone—60 g/l, glucose—100 g/l. The rate of feeding the replenishment was such as to provide a rate of growth of the culture μ=0.03. After achievement of ID50, equal to 280 optical units, the content of AFP in the CL was analyzed.

The relative and total content of AFP in the CL of high-density cultures of YB723/pKX was determined as described above in example 4. In the case of culturing in high-density mediums, the content of rAFP in the CL according to IFA data reached 70 mg/l.

EXAMPLE 7

Isolation and Characterization for Recombinant Human AFP from CL of a Strain Producer YBS723/pKX Isolation of rAFP from the CL of the strain procures YBS723/pKX was carried out as described earlier (Dudich et al., 1999, Biochemistry, 38: 10406-10414) with slight changes. The cultural liquid was concentrated from 31 to 200 ml by ultrafiltration on a concentrating cell "millpore" and dialyzed against 0.005M Tris-HCl, a pH 7.5, 0.1 M NaCl buffer, 4° C., then centrifuged for 0.5 hours at 10 000 rpm.

Ion exchange chromatography. The supernatant obtained after centrifugation was applied onto an ion exchange column DEAE-Sepharose Fast Flow (Pharmacia, 27×4 cm), balanced with 0.01 M Tris-HCl, pH 7.5, 0.1 M NaCl. The components not bond to sorbent were washed from the column with a starting buffer, while the elution of the desired product was carried out by 0.2M of NaCl in a Tris-HCl buffer, pH 7.5 at a rate of 1 ml/min.

Affinity chromatography. The fractions comprising rAFP were combined, the concentration of NaCl was brought to 0.5M and applied to an affinity column with Sepharose CL-4B conjugated with polyclonal anti-AFP rabbit antibodies, which was balanced with 0.05M Tris-HCl, pH 7.5 and 0.5M NaCl. After the output of the protein not bonded to the antibodies of the proteins, the absorbed rAFP was eluted with 0.005M HCl. The peak of the output of the material upon achievement of pH from 5.0 to 3.5 was determined by absorption at 280 nm. The solution of rAFP was neutralized to pH 7.5 by the addition of a 2M solution of Tris-HCl, pH 7.5.

Gel chromatography. Further purification of rAFP was carried out by gel chromatography on a column with Sephacryl S-200 (1.8×70 cm) in a 0.1 M phosphatebuffer, pH 7.0; 0.15M NaCl, at a rate of 0.5 ml/min. The solution of purified rAFP was concentration in a cell "Amicon" (membrane YM-30) under the pressure of nitrogen.

Analysis of samples. The identification and purity of the obtained rAFP preparation were controlled by methods of gel electrophoresis according to Lammly in 12.5% SDS-PAGE with β-mercaptoethanol with subsequent coloring by Coomassie (FIG. 4A), Western-blot analysis on a PVDF-membrane with a titer of primary antibodies 1:1500 and secondary 1:5000, dot-blot on a Hybond ECL-nitrocellulose membrane (FIG. 4B), IFA.

Determination of the concentration of the protein in the solution was carried out in accordance with the Bredford method, using a standard solution of embryonal AFP as the control, and also spectrophotometrically at 278 nm, taking the coefficient of extinction $E_{1\%278nm}=0.53$ into account.

EXAMPLE 8

Determination of Biological Activity of Recombinant Human AFP In Vitro

Figure 5:
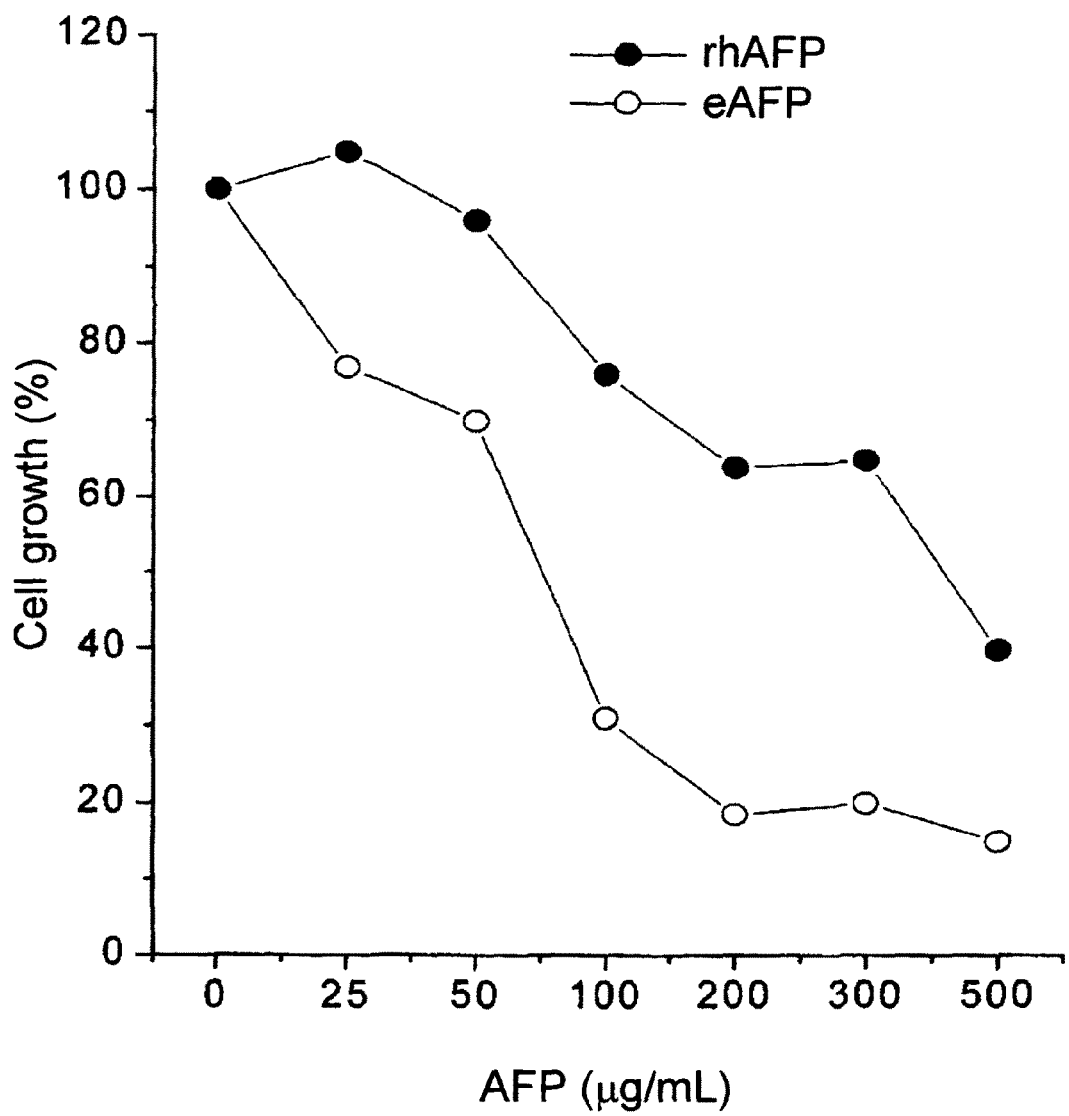
FIG. 5 shows a dose dependence of the proliferation of B-cellular Raji lymphoma cells on the AFP concentration for two different samples of purified AFP, which are obtained from embryonic serum eAFP and recombinant rAFP, that is expressed by yeast strain producer *Saccharomyces cervisiae* YBS723/pKX. Proliferation of the cells was measured by [$H^3$]-thymidine incorporation and expressed in percentage of inhibition of growth in experimental cultures after 12-hour incubation with AFP in respect to a control without activities.

The functional activity of rAFP and the modified forms thereof were determined according to its capability of suppressing the growth of cells of B-cellular lymphoma Raji in the culture in vitro, as earlier described (Semenkova, L. 1997, Tumor Biol. 18, 261-274; Dudich E. I., et al., 1998, Tumor Biol. 198, 30-40). Preliminarily washed by a fresh medium, Raji cells were placed into each cell of a 96-alverolar plate according to $5 \times 10^3$ in 0.1 ml of a medium RPMI-1640 in the presence of a 10% fetal calf serum, then different doses of AFP were added for 12 hours. Proliferation of the cells was measured by a standard method by the introduction of [$H^3$]-thymidine during the last 4 hours of culturing. For comparison, the dose-dependent reactivity was studies for two samples of AFP of embryonal origin embrAFP and yeast rAFP (FIG. 5). It is evident that both preparations manifest an expressed cytostatic activity in respect to these cells. Similarly, in order to determine the activity to preparations on the base of AFP in vitro, any other lines of cancer cells may be used that are sensitive to the suppressive action of AFP, such as human hepatocarcinoma HepG2, breast cancer MCF-7, prostate cancer LnCap, myeloblastoma U-937 and others (Semenkova, L. 1997, Tumor Biol. 18, 261-274; Dudich E. I., et al., 1998, Tumor Biol. 198, 30-40).

EXAMPLE 9

Use of Recombinant AFP as Anticancer Preparation

Anticancer preparations on the base of rAFP and of modified forms thereof may be used for inhibition of the growth of malignant neoplasms, such as primary or metastatic cancer of the liver, blood cancer (leucosis, myeloblastoma, lymphoma), breast cancer, prostate cancer. In order to determine the sensitivity of tumor cells to rAFP, it is possible to use different methods both in vitro and also in vivo. The method of determining activity in vitro is described in the preceding example 8. In order to determine the oncosuppressive action of preparations on the base of AFP in vivo, animal models may be used, for example Nude mice with subcutaneously or intraperitoneally implanted human lines of cancer cells, such as Raji, HepG2, LnCap, MCF-7 and others. For example, cells of B-cellular lymphoma Raji were administered subcutaneously in an amount of 1-5×10$^6$ per mouse. Administration of the rAFP and derivatives thereof was begun 7 days prior to implantation of tumor cells intraperioneally or intravenously in an amount of 1-10 mg/kg. The physiological buffered solution (PBS) was used as a control. The size of the tumor was evaluated by daily measurements with the aid of a micrometer.

TABLE 1

Results of tests for AFP on models of Nude line mice implanted with cells of B-cellular lymphoma Raji

| Number of animals | Dose of AFP per injection | Method of administration | Result |
|---|---|---|---|
| 10 | 1 mg | Intraperitoneally, daily for 20 days | 2-stabilization 5-50% inhibition 3- tumor did not develop |
| 5 | PBS | Intraperitoneally, daily for 20 days | 10-100% development of tumor |
| 10 | 0.5 mg | Intraperitoneally, daily for 20 days | 2-stabilization 5-50% inhibition 3 -tumor did not develop |
| 10 | 2 mg | Intraperitoneally, daily for 20 days | 2-stabilization 5-50% inhibition 3- tumor did not develop |

Figure 6:
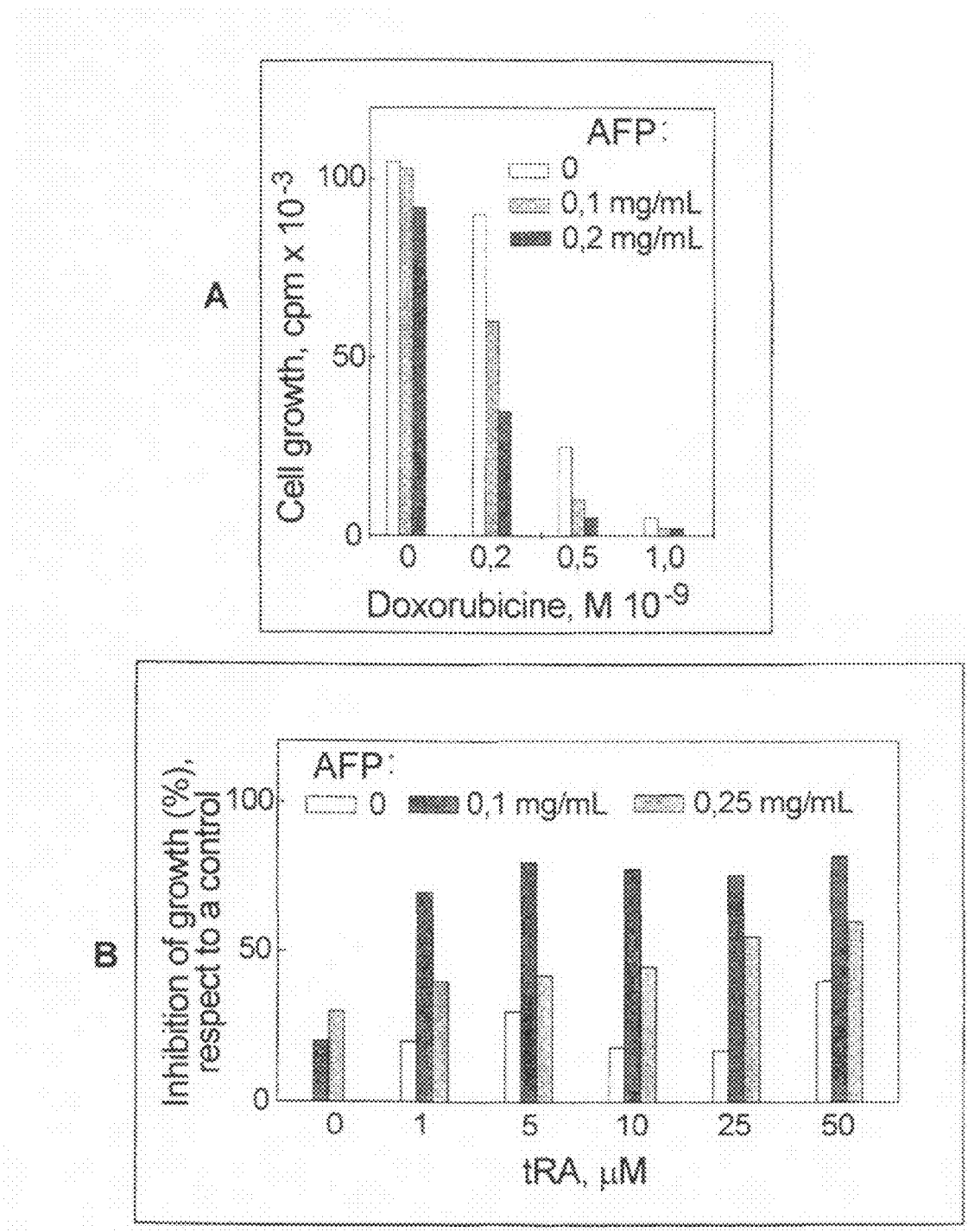
FIG. 6 demonstrates: (A) synergistic enhancement of oncosuppressive action of doxorubicine in respect to myeloblastoma U937 cells with the combined use with rAFP according to the instant invention;
(B) synergistic enhancement of the general oncosuppressive effect with combined use of rAFP according to the instant invention and retinoic acid (pro-vitamin A, acid). Proliferation of the cells was measured by $H^3$]-thymidine incorporation and expressed in percentage of inhibition of growth in experimental cultures after 12-hour incubation with AFP in respect to a control without additives.

The method of administering preparations on the base of yeast rAFP or derivatives thereof may also comprise therein the administration of chemotherapeutic preparations simultaneously or sequentially. The following may be presented as examples of such chemotherapeutic preparations: doxorubicin, vincristine, fluorouracil, metatreaxate, actinomycin D, mitomycin C, tamoxifen, flutamid, vincrsitine, vinblastine, cyclosporine, retinoids, carotenoids, and others. Usually, a chemotherapeutic preparation may be administered in standard dose or in suboptimum doses, below the usual therapeutic. The effect of the combined action of rAFP and doxorubicin (A) and rAFP and all-trans-Retinoic acid (tRA) is presented as an example in FIG. 6. In the case of simultaneous administration of the preparations, synergic oncosuppressive action in the case of use of suboptimum doses is observed.

EXAMPLE 10

Combined Therapy with rhAFP/Doxorubicin of Syngeneic Leukemia in BDF1 Mice in vivo We demonstrated earlier that oncofetal marker alpha-fetoprotein (AFP) activates apoptosis in tumor cells by blocking of XIAP activity [Dudich, E. et al. (2006) FEBS J., 273:3837-3849; Semenkova L N et al. (2003) Eur. J. Biochem. 270: 4388-4399]. Human recombinant AFP (rhAFP) was isolated from the culture medium of yeast-producer S. cerevisae and used to study its tumor-suppressive effects in vitro and in vivo both in monotherapy and combined regimens.

We have studied the effect of combined treatment with AFP+Dox of acute leukemia in mice BDF1 with transplanted intrapleurally syngeneic P388 leukemia cells. BDF-1 mice (84 male, 28 mice per treatment) were implanted with lethal dose of 12×10$^6$ syngeneic leukemia cells P388 in the pleural region. Animals were subjected to monotherapy with Dox and combined therapy with rhAFP/Dox upon simultaneous single injection of drugs in various doses. Animal survival was compared over 30 days.

Results: Combined treatment of P-388 cells in vitro with rhAFP/Dox resulted in synergistic enhance of the total tumor suppressive effect and drastic enhance of the amount of apoptotic cells (>80%) at suboptimal doses of both compounds. Median animal survival was 6.5 days for placebo, 20.5 [15 to 22] days for monotherapy with Dox and 27.7 [19 to >30] days for combined rhAFP/Dox therapy. Effectiveness (T/C %) in rhAFP/Dox group was significantly higher than in monotherapy Dox group.

TABLE 2

Results of treatment of the BDF1 mice with transplanted synergeneic acute leukemia P388 with doxorubicin and rhAFP/doxorubicin

| Treatment | Dose (mg/kg) | T (Survival, days) | T/C % | survival more 30 days |
|---|---|---|---|---|
| Placebo | | 6.5 [6.2 ÷ 6.8] | 100 | 0 |
| Dox | 1.0 | 15.5 [13.9 ÷ 17.1] | 238 | 0 |
| Dox | 3.0 | 19.7 [17.0 ÷ 22.4] | 303 | 0 |
| Dox | 5.0 | 20.5 [15.7 ÷ 21.8] | 315 | 0 |
| rhAFP | 25.0 | 7.7 [6.4 ÷ 9.0] | 118 | 0 |
| Dox/rhAFP | 1.0/25.0 | 18.8 [17.1 ÷ 20.5] | 289 | 0 |
| Dox/rhAFP | 3.0/25.0 | 20.5 [19.2 ÷ 21.8] | 315 | 0 |
| Dox/rhAFP | 5.0/25.0 | 27.7 [20.4 ÷ 30.0] | 426 | 3/7 |

Conclusions: 1) Combined treatment with single injection of rhAFP/Dox resulted a significant enhance of the survival rate and effectiveness, resulting in complete remission in >40% animals as compared to monotherapy with Dox; 2) rhAFP operates by sensitization of tumors to apoptotic signals resulting in synergistic enhance of effectiveness and decrease of effective dose of Dox.

EXAMPLE 11

Protective Effect of Monotherapy with rhAFP Against Human Hepatoma Xenografts Transplanted in Nude Mice in vivo To study tumor-suppression upon monotherapy with rhAFP we used in vivo model of human hepatoma xenografts in Nude mice. Balb C/Nude mice 8/group were implanted with 12×10$^6$ human hepatoma cells HepG2 s/c. rhAFP 10 mg/kg was injected i/p 9 times each 48 hrs during 16 days. Effectiveness of treatment was assessed by measuring and weighting of the tumor at the 30$^{th}$ day of experiment and by comparison of the quantity of mice with tumor during time of observation.

Results: Without treatment, tumors were determined at 5$^{th}$-7$^{th}$ day after transplantation. In the experimental rhAFP group, tumors did not grow in the period of treatment and became detectable at the 25$^{th}$-27$^{th}$ day after beginning of the experiment. Monotherapy with rhAFP was resulted in the notable protective effect and significant suppression of tumor growth reaching of 90% inhibition of total tumor weight relatively to untreated control. Treatment of human hepatoma cells HepG2 in vitro with rhAFP induced dose-dependent growth suppression and apoptosis.

Conclusions: Monotherapy with rhAFP prevented development of human hepatoma xenografts in Nude mice.

EXAMPLE 12

Figure 8A:
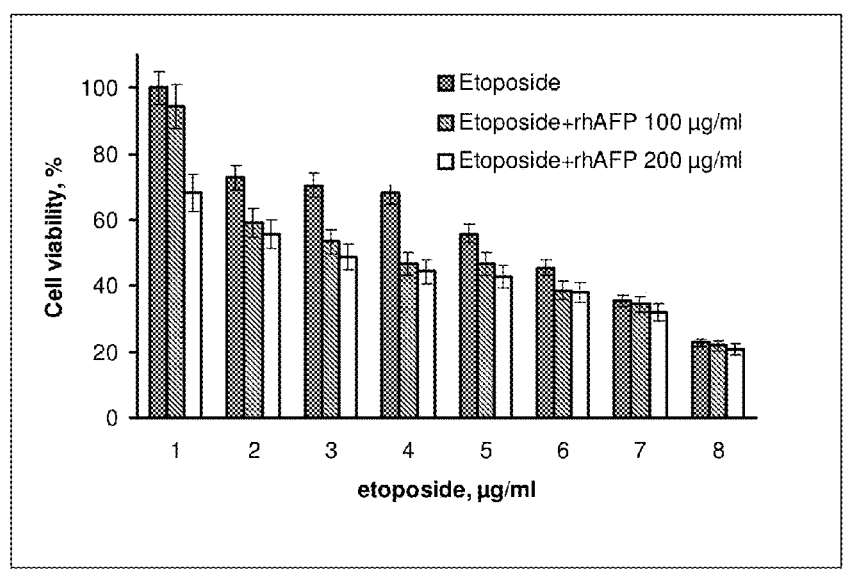
FIG. 8 (A-C) shows effect of combined 48-hrs treatment with various doses of rhAFP/doxorubicin (8B); rhAFP/cysplatin (8C), rhAFP/etoposide (8A) of human breast cancer cell MCF-7 in vitro. Cell proliferation was assessed by H3-thymidine incorporation assay or by MTT technique.
Figure 8B:
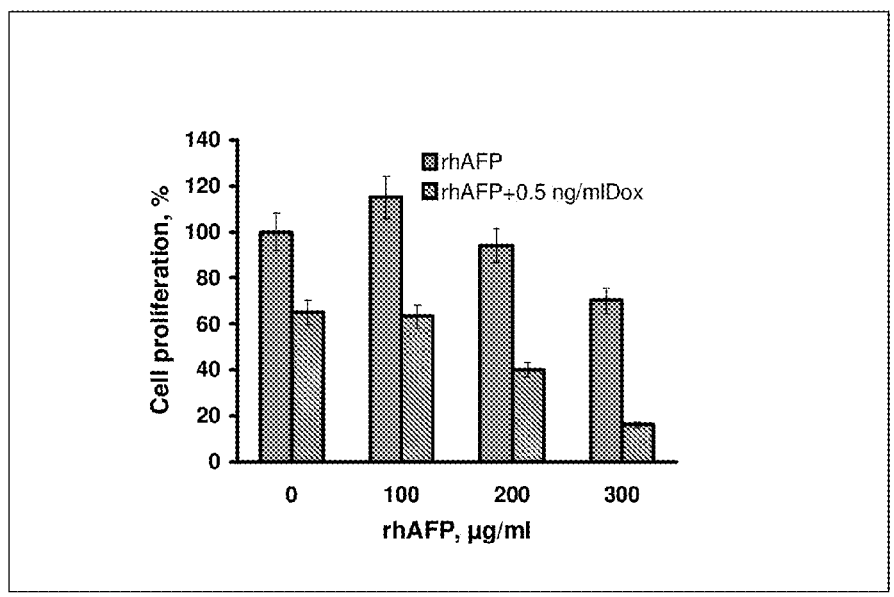
Figure 8C:
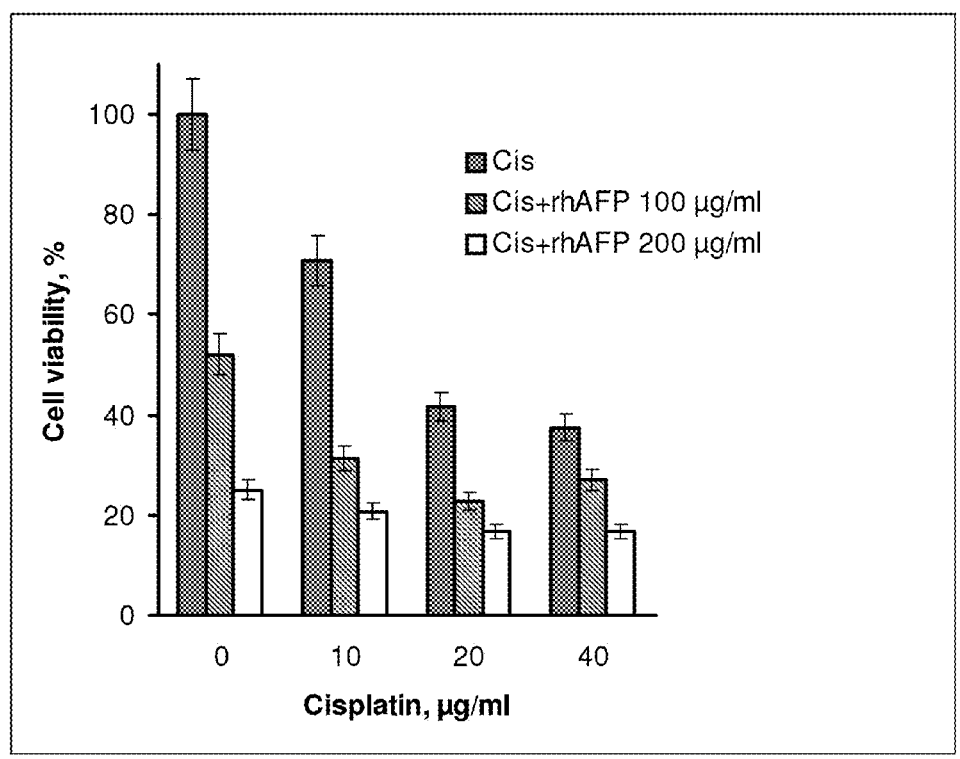

Synergistic Tumor-Suppressive Effect of Combined Treatment of Human Breast Cancer Cells in vitro with Combinations of rhAFP with Doxorubicin, Cysplatin, Etoposide, Metatrexate Human breast cancer cells MCF-7 were plated onto 96-well plastic wells (Costar) in 10$^4$ cells/ml in DMEM medium with addition of 2% fetal calf serum and were treated during 72 hrs with one of chemotherapeutic agents: doxorubicin, cysplatin, etoposide, metatrexate or those with addition of 0.1 mg/ml of rhAFP. Cytotoxic effect was estimated by MTT assay or H3-thymidine incorporation assay. It was observed synergistic enhance of the total tumor-suppressive effect in suboptimal doses of all agents in the presence of AFP (FIG. 8). These data indicate that combined chemotherapeutic regimen by using various cytotoxic agents including doxorubicin, cysplatin, etoposide, metatrexate together with rhAFP results in significant synergistic tumor-suppression.

Figure 9:
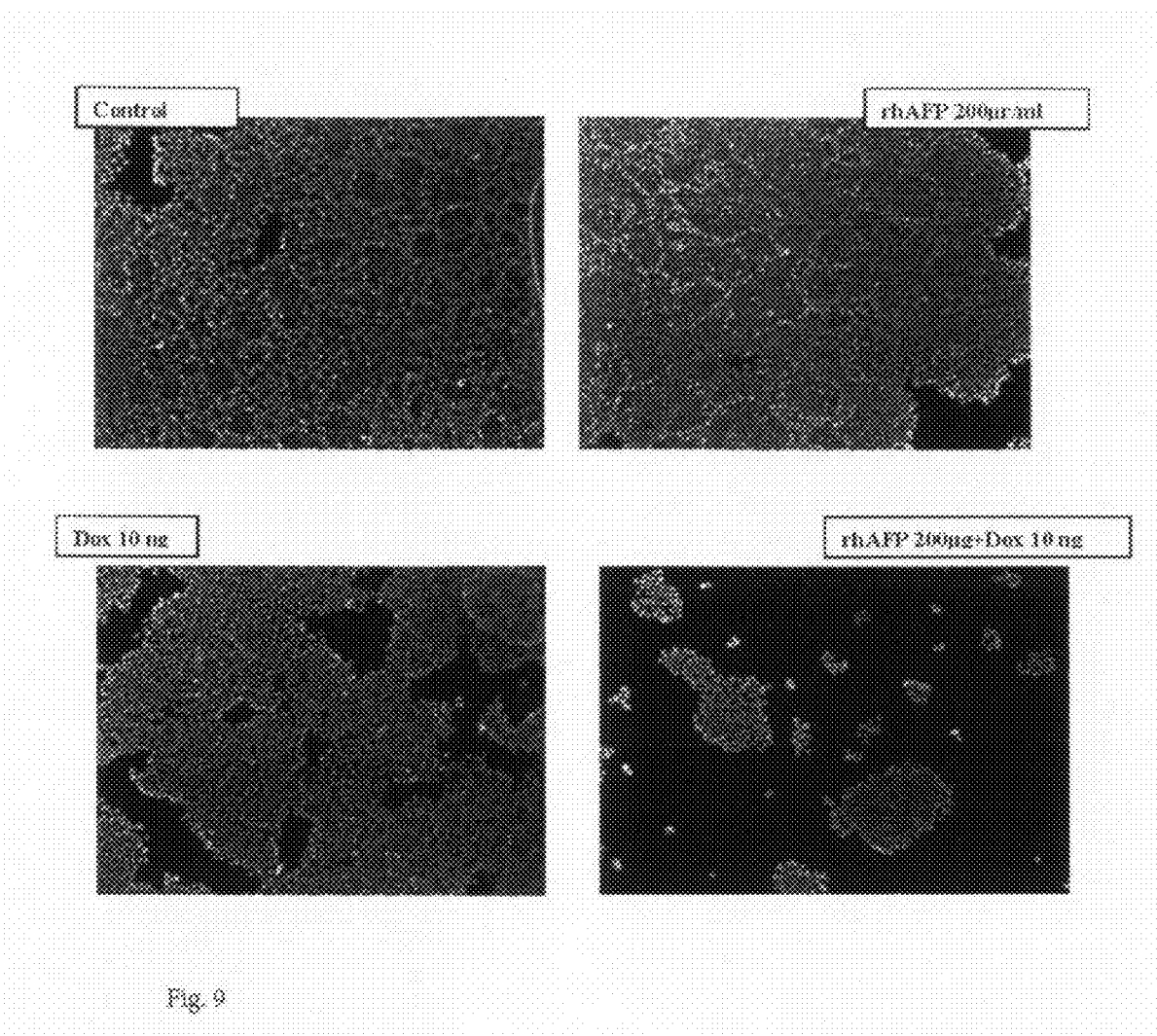
FIG. 9 shows microscopic image of cytotoxic effect after combined treatment with suboptimal doses of doxorubicin and rhAFP against human breast cancer cells MCF-7 in vitro demonstrating effectiveness of rhAFP/Dox therapy. Cells were plated at 80% of confluence and thereafter treated with rhAFP/Dox for 48 hrs. Cells were visualized in fluorescence microscope Axioplan (Zeiss) in 100-fold magnification after staining with crystal violet.

FIG. 9 shows microscopic image of direct cytotoxic effect of combined treatment with suboptimal doses of doxorubicin and rhAFP against human breast cancer cells MCF-7 in vitro demonstrating effectiveness of rhAFP/Dox therapy.

Our data shows that rhAFP sensitizes tumor cells to chemotherapy by blocking of inhibitory signaling with inhibitor of apoptosis proteins XIAP overexpressed in tumor cells [Dudich E. et al. (2006) FEBS J., 273:3837-3849].

EXAMPLE 13

Synergistic Immunosuppressive Effects of Cyclosporine A and rhAFP

Figure 10A:
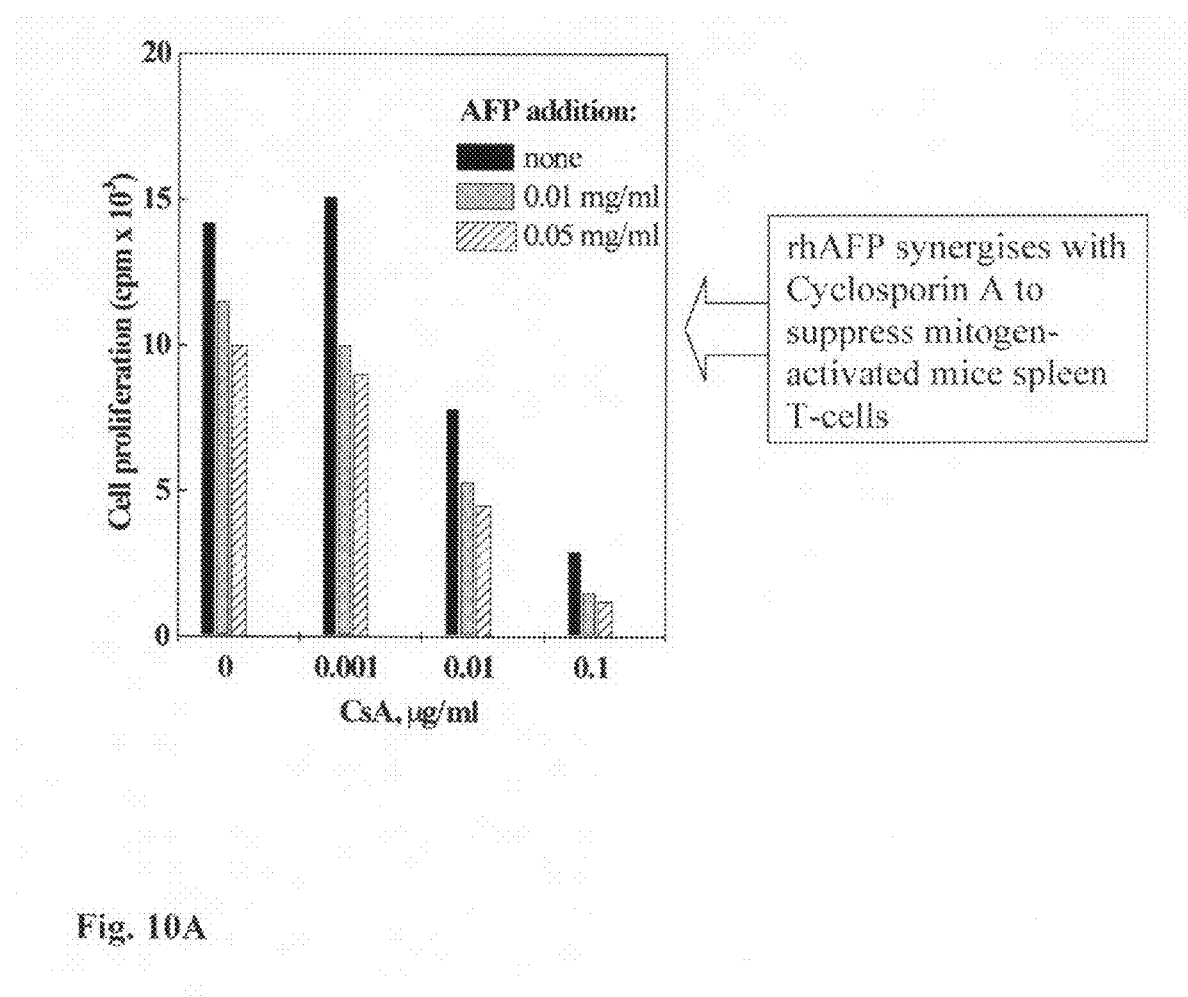
FIG. 10 (A-D) shows the combined synergistic suppression of the PHA-mediated thymocyte proliferation in vitro induced by combined treatment with rhAFP and cyclosporineA (A); the combined synergistic suppression the proliferation of alloantigen-activated mice spleen cells induced by combined AFP/CsA treatment (B); rhAFP-induced cancellation of the cytotoxic effects of CsA treatment of resting mouse T-cells (C); synergistic inhibition of IgG and IgM antibody production by SRBC-activated mouse B-cells induced by combined treatment with rhAFP/CsA. Doses of rhAFP and CsA are shown in the pictures. The description of the experiment is given in Example 12.
Figure 10B:
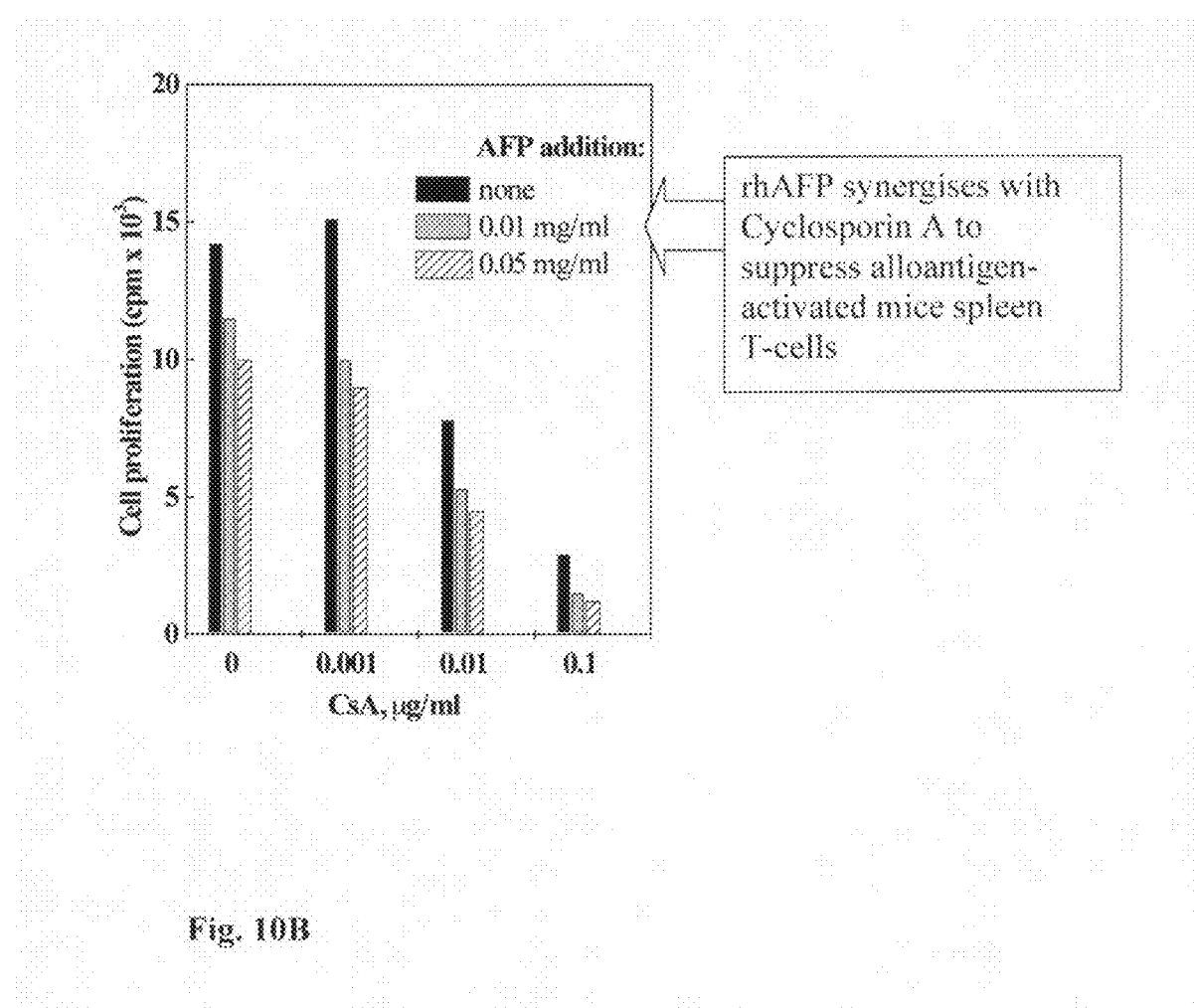
Figure 10C:
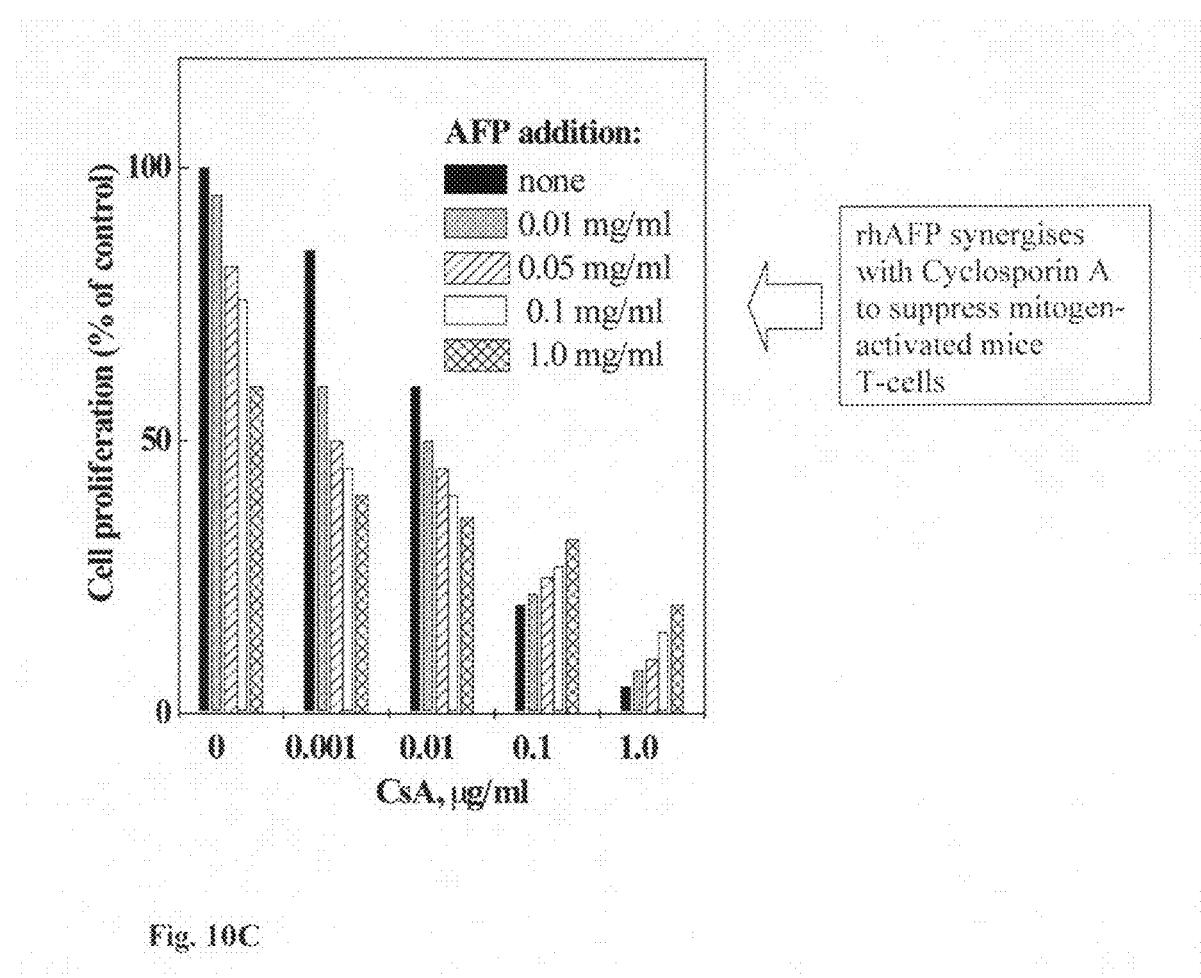
Figure 10D:
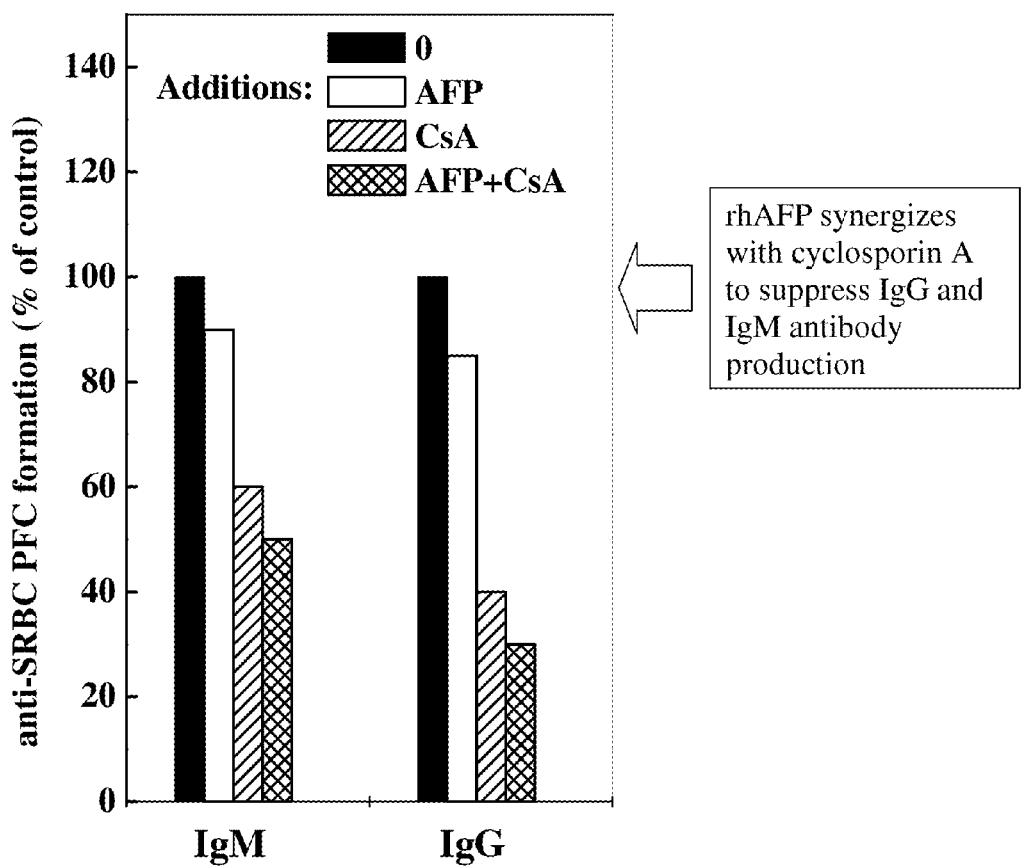

To study combined effect of AFP and CsA on the PHA-mediated thymocyte proliferation in vitro mouse CBA thymocytes were pre-incubated for 48 hrs with 1.5 μg/ml of PHA and thereafter various doses of rhAFP and CsA were added to thymocytes for the next 24 hrs and to thereafter assessed for their proliferation (FIG. 10A). Combined effect of AFP/CsA on the proliferation of alloantigen-activated mice spleen cells was estimated by treatment of responding CBA splenocytes with mitomycin C-treated allogeneic C57BL/6 splenocytes in the presence of various doses of rhAFP and CsA for 5 days (FIG. 10B). Control resting splenocytes CBA were treated for the same time with combination of rhAFP/CysA (FIG. 10C). Cytostatic effects were assessed by monitoring of cell proliferation by [$^3$H]-thymidine incorporation.

Combined effect of AFP/CsA (50 μg/ml/10 ng/ml) and of the same doses of these compounds alone on the sheep red blood cells SBRC-specific IgG and IgM humoral immune response in vitro. Spleen cells were obtained from CBA mice preliminary primed with SRBC and additionally stimulated with SRBC in the presence of AFP/CsA for the next 5 days in vitro. Thereafter IgG and IgM plaque forming cells (PFC) were determined by direct and indirect PFC assay. The results of these experiments are shown on FIG. 10 D.

FIG. 10 shows effect of combined rhAFP/CsA treatment on the proliferation of PHA-activated CBA thymocytes (TC). Stimulated by PHA thymocytes showed distinct dose-dependent growth suppression in response to AFP. Addition of CsA together with AFP significantly enhanced total immunosuppressive effect, demonstrating more than two-fold more significant growth suppression in comparison with that induced by AFP or CsA alone.

Malignant human immune cells Jurkat (T-Lymphoma) were also subjected to the combined treatment with CsA/rhAFP. It was observed significant synergy in total growth suppressive activity (data not shown).

Combined effects of AFP and CsA on the various types of activated immune cells and also on the different tumor cell lines cultivated in vitro was investigated. It was revealed that:
(i) Low doses of AFP significantly increased low-dose-CsA-mediated immunosuppressive effects in T-cells activated with mitogens or alloantigens;
(ii) AFP operates as a highly selective modulator of the CsA-mediated immunosuppressive signals by inducing of targeting suppression of activated cells only, but does not suppress resting immune cells;
(iii) Taking into account that AFP simultaneously attenuates cytotoxic effects of CsA in resting T cells by decreasing of the effective concentration of free CsA in the cell surrounding, it could be concluded that AFP significantly decreases unspecific toxicity;
(iv) Our data demonstrate, that AFP could serve as a highly effective compound of the targeting immunnosuppressive multicomponent drugs on the base of CsA to deliver immunnosuppressants into the activated cells, expressing AFP-receptors and simultaneously to diminish unwished side toxic effects against resting cells;
(v) Data, showing the combined growth-suppressive effects of AFP/CsA in Jurkat cells, suggest the possible use of suboptimal CsA doses in combination with AFP to suppress growth of leukemic cells whereas toxic and suppressive effects against normal resting cells will be negligible.
(vi)

TABLE 3

Targeting modulation of CsA effects by human AFP.

| Drug Description | Dose | Activity in vitro | Possible Medical use | Unwished Side Effects | AFP-mediated modulation of CsA effects |
|---|---|---|---|---|---|
| CsA (High doses) | 0.1-1.0 μM | 1. Apoptosis in thymocytes; 2. Hepatocytes, 3. kidney cells, 4. Lymphoblastoma cells | 1. Preventing of graft rejection at organ transplantation; 2. Treatment of autoimmune diseases 3. Cancer Therapy | Hepatotoxicity, Hyperbilirubinemia; Cholestasis in heart transplant; Immunosuppression. | — |

TABLE 3-continued

Targeting modulation of CsA effects by human AFP.

| Drug Description | Dose | Activity in vitro | Possible Medical use | Unwished Side Effects | AFP-mediated modulation of CsA effects |
|---|---|---|---|---|---|
| CsA (Low doses) | 0.01-0.1 µM | Cytostasis of immune cells; Cytostasis of leukemic cells. | No use | No effects | — |
| CsA + AFP (High doses) | CsA: 0.1-1.0 µM AFP: 0.1 µM | Abrogation of the high dose CsA-induced apoptosis for normal cells in vitro; Sensitization of resistant cells to CsA | 1. Cancer Therapy; 2. Abrogation of CsA resistance in cancer cells; 3. Transplantaion; 4. Autoimmune disease treatment. | Significant decrease of unspecific toxicity | Targeting enhance of total effect against malignant cells |
| CsA + AFP (Low doses) | CsA: 0.01-0.1 µM AFP: 0.1 µM | Synergistic enhance of the total immuno-suppression | 1. Cancer Therapy; 2. Abrogation of CsA resistance in cancer cells; 3. Transplantaion; 4. Autoimmune disease treatment. | Abrogation of unspecific toxicity | Synergistic targeting enhance of total suppressive effect |

EXAMPLE 14

Use of rhAFP for Stimulation of Growth of Adult Stem Cells

Human mesenchymal stromal/stem adipose tissue cells (ATSC) were isolated either from liposuction aspirates or from products of the fat deposit removed during the cosmetic surgery. The tissue was mechanically split to the fragments of several cubic millimeters. A suspension of tissue was mixed with type I Collagenase (200 U/ml) and Dispase (30 U/ml) (Sigma) in solution of 50% DMEM (Sigma, D-5523), 50% F12 (Sigma, N-6760), 1% BSA (Sigma), /100 U/ml penicillin and 100 U/ml ampicilline in 1:1 v/v and incubated for 1 hr at 37° C. to with mixing, following by filtering through 40 µm membrane (BD Falcon). The suspension was centrifuged 5 min at 200 g, upper layer was removed, and pellet consisting of separate non-adipose cells was treated by erythrocyte lysis buffer (154 mM $NH_4Cl$, 10 mM $KHCO_3$, 0.1 mM EDTA) during 5 min at 37° C., following by 5 min centrifugation at 300 g. Cell pellet was resuspended in DMEM/10% FBS. Resulting cells were cultured in the same medium in plastic flasks in $CO_2$ incubator (37° C., 5% $CO_2$). When reaching confluence, the cells were passaged by treatment the cell monolayer with 0.25% trypsin/0.02% EDTA. For the purpose of long-time storage, the cells were frozen in the culture medium supplemented by 15-20% FBS and 10% DMSO. Adipose cells were cultivated in DMEM/F12 medium with the addition 10% FBS и 0.1% ECGF on 60 mm Petri dishes at 37° C. and 5% $CO_2$. For the passages 0.25% trypsin/0.02% EDTA. solution was used. For the purpose of long-time storage, the cells were frozen in the culture medium supplemented by 15-20% FBS and 10% DMSO. Adipose tissue stem cells (ATSC) were cultivated in DMEM/F12 medium with the addition 10% FBS и 0.1% ECGF on 60 mm Petri dishes at 37° C. and 5% $CO_2$. For the passages 0.25% trypsin/0.02% EDTA solution was used. For the purpose of long-time storage, the cells were frozen in the culture medium supplemented by 15-20% FBS and 10% DMSO.

Human donor ATSC were isolated and cultivated as described above, the cells from 2-4 passage were taken in the study. ADSC ($3 \times 10^4$) were plated in flat-bottom 96-well plates (Costar, USA) in complete medium with 10% FCS, after 18 h the medium was changed onto the medium with 5% human sera and cells were treated with increasing amounts of rhAFP (0-500 µg/ml) for 24 h. The direct effect of rhAFP on proliferation of ATSC was measured by $[H^3]$-thymidine incorporation. For the last 4 h 1 µCi of methyl-$[H^3]$-thymidine was added to the cultures. AFP treatment ((0-500 µg/ml) resulted in enhanced proliferation of ATSC when compared to untreated control (Table 4). Maximum effect was obtained for 300 µg/ml of rhAFP (50%).

TABLE 4

Stimulation by rhAFP of growth of adipose derived adult stem cells in vitro.

| | Cell proliferation (cpm × $10^3$) | | |
|---|---|---|---|
| AFP (mg/ml) | 0 (control) | 0.100 | 0.300 |
| 2 passage | 17.8 ± 6.4 | 20.7 ± 0.7 (+16%) | 25.8 ± 4.1 (+44%) |
| 3 passage | 16.5 ± 1.5 | 17.7 ± 5.3 (+7%) | 22.4 ± 1.4 (+35%) |
| 4 passage | 0.83 ± 0.1 | 1.0 ± 0.08 (+20%) | 1.2 ± 0.24 (+50%) |

The data obtained demonstrate that rhAFP operates as a growth factor for adult stem cells and can be employed as a component of culture medium for in vitro cultivation of autological stem cells for auto-transplantation and regenerative stem cell therapy.

EXAMPLE 15

Use of Recombinant AFP for Simulation of the Growth of Stem Cells

The primary culture of embryonal fibroblasts of the lung and human retina was obtained by treating with 0.25% trypsin solution corresponding tissues of 5-10 week embryos obtained after legal abortions. The cells were cultures in an RPMI-1640 medium in the presence of a 10% calf fetal serum (CFS). The cytostatic activity of AFP was measured as earlier described (Semenkova, L. 1997, Tumor Biol. 18, 261-274; Dudich E. I., et al., 1998, Tumor Biol. 198, 30-40). Cells in an amount of $4 \times 10^4$ in a 0.15 ml medium were intensively washed with a fresh to medium and placed in each cell of a 96-lune plate, then different doses of AFP were added and cultures 24 hours. Proliferation of the cells was measured by a standard method by the inclusion of [$H^3$]-thymidine during the last four hours of culturing.

EXAMPLE 16

Figure 12:
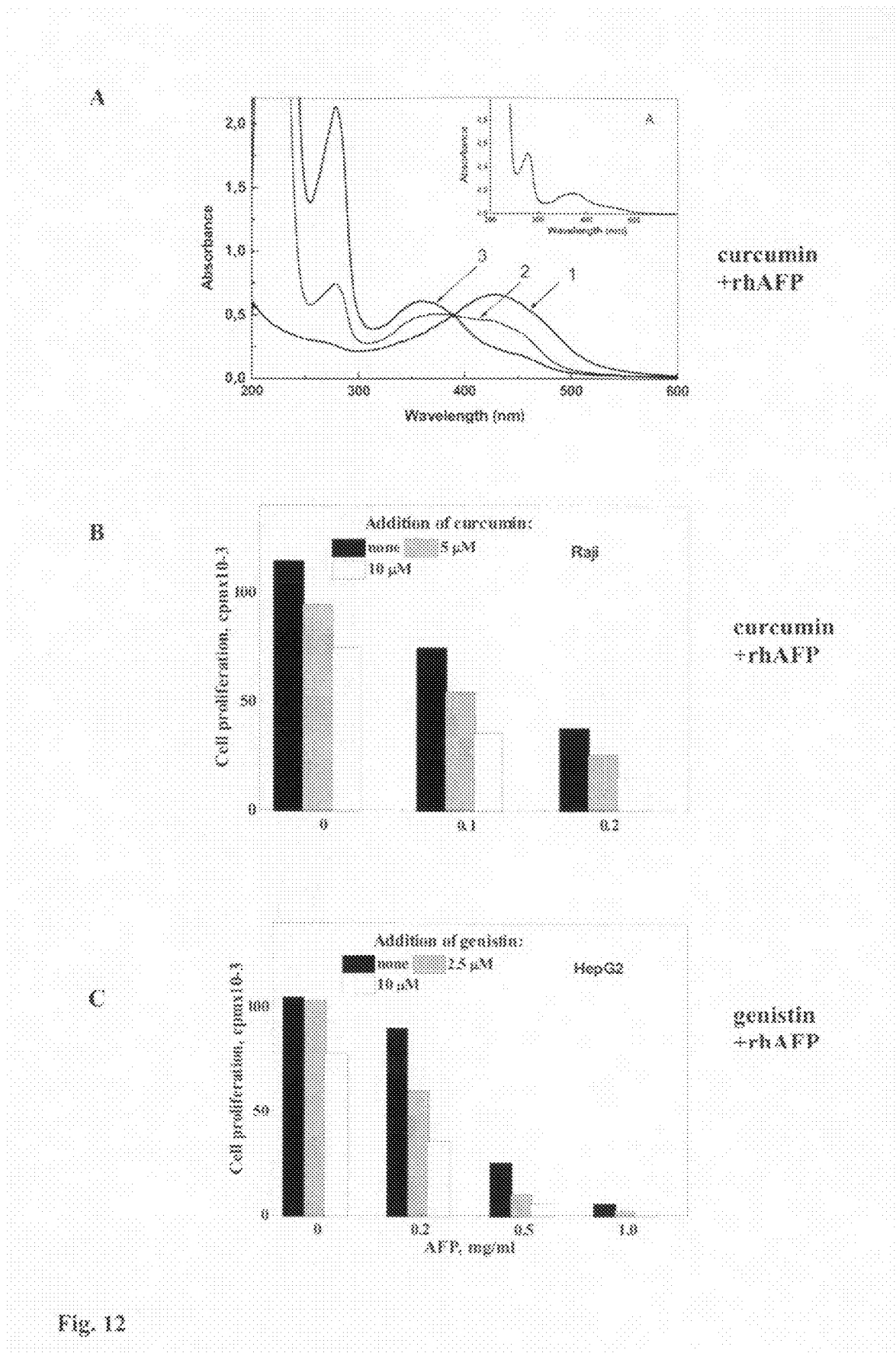
FIG. 12 shows the experimental demonstration of formation of non-covalent complex of rhAFP and curcumin (A) with demonstration of synergistic anti-tumor effects of combined administration of rhAFP with curcumin (B) and genistin (C). Absorption spectra of aqueous solutions containing 30 µM of curcumin and various doses of rhAFP: (1) 30 µM of curcumin; (2) 30 µM of curcumin+20 µM rhAFP; (3) 30 µM of curcumin+40 µM rhAFP. Panel at the top (A): absorption spectra of non-covalent complex of rhAFP/curcumin after chromatography through a column with Sephadex G-25.

Synergistic Tumor-Suppressive Effect in vitro for Combinations of rhAFP with Plant-Derived Tumoricidal Compounds, Flavonoids, Isoflavonoids, Flavons, Flavanones, Isoflavanones AFP can take small hydrophobic ligand molecules to deliver them to developing cells expression AFP-receptors, including stem cells and tumor cells, contributing significantly to physiological functions and acts as carrier protein. Phytochemicals are nonnutritive components of plants that are currently being studies in chemoprevention and combined therapy of cancer. Curcumin is the active component of tumeric, it has been shown to possess anti-inflammatory, antioxidant and antitumor properties. Other plant-derived tumoricidal compounds—flavonoids, isoflavonoids, flavons, flavanones, isoflavanones have been widely investigated for their ability to suppress tumor growth in vitro. Some of them display significant homology with steroids and mimic reveal antagonistic or agonistic activity in mammals. Ability of AFP to bind isoflavanoids was documented by various researches (Deutsch H. F, 1991, Adv. Canc. Res. 56, 253-312). We have documented the ability of rhAFP to form noncovalent complexes with plant derived compounds curcumin and genistin and to synergize in suppression of growth if various types of tumor cells in vitro. By steady-state absorption measurements it was demonstrated the formation of equilibrium noncovalent complexes of rhAFP and curcumin (FIG. 12 A). The absorption spectra of solutions containing curcumin and rhAFP were followed keeping concentration of curcumin constant 30 µM and rhAFP varied from 5 µM to 40 µM. FIG. 12A curve 3 shows absorption spectra for pure 30 µM curcumin dissolved in Et-OH followed with 1:5 dilution with phosphate buffer pH 7.4, curve 2 shows absorption spectra of 20 µM of rhAFP and 30 µM curcumin, and curve 3 shows spectra of 40 µM of rhAFP and 30 µM curcumin. FIG. 12 A gives the absorption spectral changes in curcumin in the presence of rhAFP in the wavelength range of 250-550 nm. It is distinctly seen, that pure curcumin has characteristic absorption spectra with maximum at about 426 nm. Whereas after addition of rhAFP the maximum of absorbance of curcumin blue-shifted from 426 to 350 nm (curve 3). These data indicate significant changes in bound curcumin microenvironment due to its binding to rhAFP. Another experiment was produced to obtain bound form of curcumin/rhAFP complex. RhAFP and curcumin were mixed in equimolar concentrations, incubated for 1 hr and subjected to chromatography on the column with Sephadex G-25 to remove unbound curcumin. Protein peak corresponding to 70 kDa was collected and absorption complex of rhAFP/curcumin was obtained (FIG. 12A, right corner at the top). This complex does not contain free curcumin and shows two distinct absorption maxima—that corresponding to protein absorbance at 280 nm, and another one corresponding to bound curcumin at 350 nm. These data shows that curcumin can form complex with rhAFP. Another series of experiments were produced to show synergistic effects of combined administration of rhAFP and plant-derived compounds curcumin and genistin in suppression of tumor cell growth. FIG. 12B, C shows that both curcumin and genistin demonstrated significant enhance of the total tumor suppressive effect upon combined treatment with rhAFP, showing high therapeutic potential for cancer treatment.

EXAMPLE 17

Use of Recombinant AFP in Cosmetology

In view of the fact that AFP has the capability to stimulate the growth of stem cells and is a growth factor for embryonic cells, its possible use is proposed for the preparation of cosmetic masks, creams and lotions. rhAFP may be used as an excipient for liposome, microsome and nanosome. In view of the fact that AFP is capable of binding hydrophobic ligands, in particular, fat-soluble vitamins, steroids, isoflavonoids, polyunsaturated fatty acids (Deutsch H. F., 1991, Adv. Anc. Res. 56, 253-312); Aussel C. & Masseyeff R. 1994, Biochem. Blophys. Res. Commun. 119: 1122-1127; Deutsch H. F., 1994, J. Tumor Marker Oncol. 9:11-14), the combined use of rhAFP with fat-soluble vitamins, such as derivatives of retinoids, carotinoids, tocoferol, vitamin D, with steroids such as derivatives of estrogens and androgens, is shown. Estradiols and others may be used as an example of such steroids.

EXAMPLE 18

Use of rhAFP for Tissue Regeneration and Repairing

Figure 11:
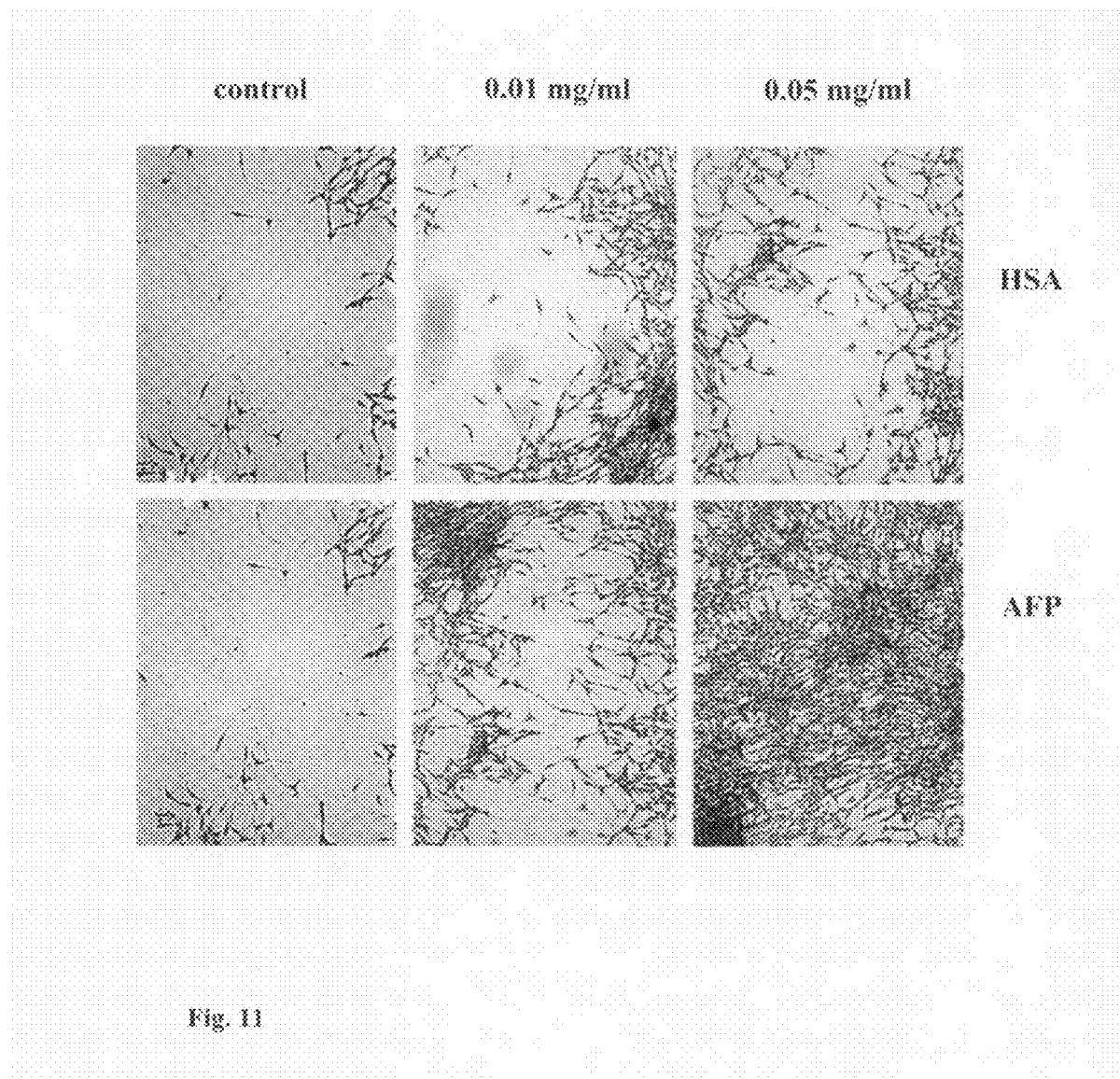
FIG. 11 shows the stimulation of regeneration potential of human umbilical vein cells (HUVEC) by rhAFP or human serum albumin. HUVECs were plated onto the gelatin-coated 24-well plates, and grown for confluence. Than monolayers were wounded by scrapper, and cells were incubated in the serum-free medium with 0.1-0.5 mg/ml of rhAFP or HSA. Healing was observed microscopically after 18-hrs incubation with HSA (top) or rhAFP (bottom) after staining with crystal violet. rhAFP significantly activated the migration of HUVEC to the wounded area.

To test ability of rhAFP to stimulate regeneration of damaged tissue we established classical wound healing assay with normal Human Umbilical Vein Endothelial Cells (HUVEC) obtained after surgical resection of human vein tissue. HUVEC cells were cultivated in DMEM/F12 medium with addition 10% FBS and 0.1% ECGF on the 60 mm Petri dishes at 37° C. at 5% $CO_2$ atmosphere. HUVECs were plated on gelatin-coated 24-well plates, and grown for confluence, than monolayers were wounded and cells were incubated in serum-free medium with 50 µg/ml rhAFP or 50 µg/ml HSA, healing was observed after 18 hrs incubation. Images of wound healing were taken after staining with crystal violet. Representative photomicrographs of cells treated with HSA (control), and cells treated with rhAFP are shown in FIG. 11. RhAFP significantly activated the migration of HUVEC to the wounded area. These data indicate that rhAFP can be used as a component of therapeutic compositions for tissue regeneration after various damage condition.

Figure 7:
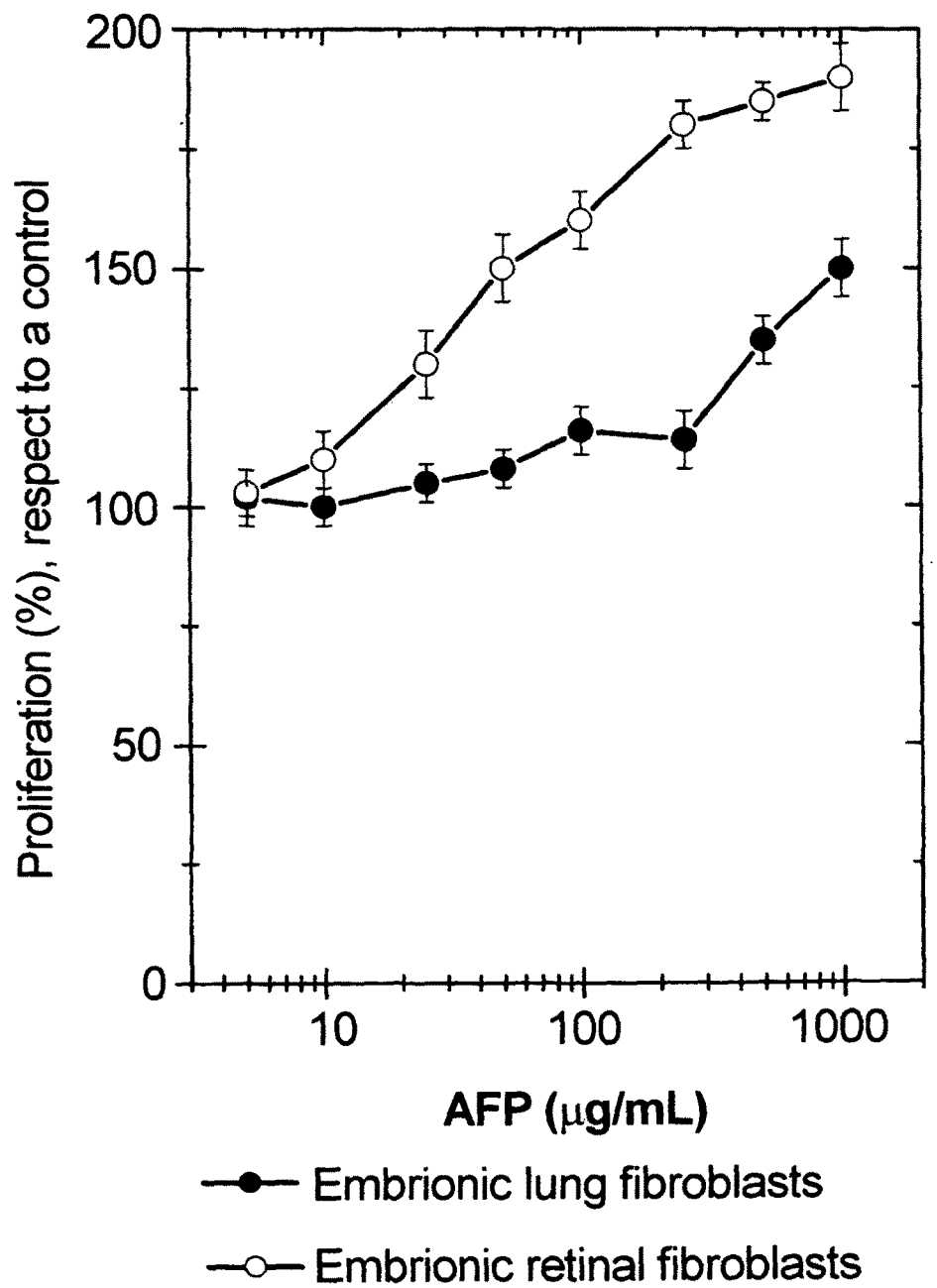
FIG. 7 shows the stimulating effect of rAFP according to the instant invention on the growth of stem embryonic cells obtained form a primary culture of cells of embryonic lung and retina. Proliferation of the cells was measured by a standard method of [$H^3$]-thymidine incorporation during the last four hours of culture and expressed in percent of the stimulation of growth in test cultures in respect of a control without AFP.

The dosage dependence of the effect of AFP on cellular growth was also studies for the primary culture of human embryoanal fibroblasts. AFP had a stimulating effect on these cells, reaching 50-90% in respect to the control (FIG. 7).

These data demonstrate potential of use of rhAFP for regeneration of skin and vascular tissues and for therapeutic cosmetics followed after traumatic and age tissue damage.

What is claimed is:

1. A secreted soluble form of recombinant mature human alpha-fetoprotein (rhAFP) comprised in a culture medium, where the concentration of the alpha-fetoprotein is at least 10 mg/l, and the alpha-fetoprotein is secreted in the culture medium by *Saccharomyces cerevisiae* cells transformed with an expression cassette comprising the nucleic acid according to SEQ ID NO: 1.

2. A culture medium comprising a secreted soluble form of recombinant mature human alpha-fetoprotein (rhAFP) in a concentration of at least 10 mg/l, wherein said rhAFP is secreted in the culture medium by *Saccharomyces cerevisiae* transformed with an expression cassette comprising the nucleic acid sequence according to SEQ ID NO: 1.

3. The culture medium of claim 2, wherein the *Saccharomyces cerevisiae* is strain YBS723.

* * * * *

SEQUENCE LISTING

<160> NUMBER OF SEQ ID NOS: 7

<210> SEQ ID NO 1
<211> LENGTH: 2556
<212> TYPE: DNA
<213> ORGANISM: artificial sequence
<220> FEATURE:
<223> OTHER INFORMATION: chemically synthesized
<220> FEATURE:

```
<221> NAME/KEY: misc_feature
<222> LOCATION: (1)..(2556)
<223> OTHER INFORMATION: pKX plasmid
<220> FEATURE:
<221> NAME/KEY: misc_feature
<222> LOCATION: (1)..(527)
<223> OTHER INFORMATION: GAL1 promoter region

<400> SEQUENCE: 1
```

| | | | | | |
|---|---|---|---|---|---|
| aagctttagc | ctaaaaaaac | cttctctttg | gaactttcag | taatacgctt | aactgctcat    60 |
| tgctatattg | aagtacggat | tagaagccgc | cgagcgggtg | acagccctcc | gaaggaagac   120 |
| tctcctccgt | gcgtcctcgt | cttcaccggt | cgcgttcctg | aaacgcagat | gtgcctcgcg   180 |
| ccgcactgct | ccgaacaata | aagattctac | aatactagct | tttatggtta | tgaagaggaa   240 |
| aaattggcag | taacctggcc | ccacaaacct | tcaaatgaac | gaatcaaatt | aacaaccata   300 |
| ggatgataat | gcgattagtt | ttttagcctt | atttctgggg | taattaatca | gcgaagcgat   360 |
| gatttttgat | ctattaacag | atatataaat | gcaaaaactg | cataaccact | ttaactaata   420 |
| ctttcaacat | tttcggtttg | tattacttct | tattcaaatg | taataaaagt | atcaacaaaa   480 |
| aattgttaat | atacctctat | actttaacgt | caaggagaaa | aaactaccat | gagatttcca   540 |
| tctatcttca | ctgcagtttt | attcgcagca | tcctccgcat | tagctgctcc | agtcaacact   600 |
| acaacagaag | atgaaacggc | acaaattccg | gctgaagctg | tcatcggtta | cttagattta   660 |
| gaagggatt  | tcgatgttgc | tgttttgcca | ttttccaaca | gcacaaataa | cgggttattg   720 |
| tttataaata | ctactattgc | cagcattgct | gctaaagaag | aaggggtatc | catggctaaa   780 |
| aggacactgc | atagaaatga | atatggaata | gcttccatat | tggattctta | ccaatgtact   840 |
| gcagagataa | gtttagctga | cctggctacc | atattttttg | cccagtttgt | tcaagaagcc   900 |
| acttacaagg | aagtaagcaa | aatggtgaaa | gatgcattga | ctgcaattga | gaaacccact   960 |
| ggagatgaac | agtcttcagg | gtgtttagaa | aaccagctac | ctgcctttct | ggaagaactt  1020 |
| tgccatgaga | agaaaatttt | ggagaagtac | ggacattcag | actgctgcag | ccaaagtgaa  1080 |
| gagggaagac | ataactgttt | tcttgcacac | aaaaagccca | ctccagcatc | gatcccactt  1140 |
| ttccaagttc | cagaacctgt | cacaagctgt | gaagcatatg | aagaagacag | ggagacattc  1200 |
| atgaacaaat | tcatttatga | gatagcaaga | aggcatccct | tcctgtatgc | acctacaatt  1260 |
| cttctttggg | ctgctcgcta | tgacaaaata | attccatctt | gctgcaaagc | tgaaaatgca  1320 |
| gttgaatgct | tccaaacaaa | ggcagcaaca | gttacaaaag | aattaagaga | aagcagcttg  1380 |
| ttaaatcaac | atgcatgtgc | agtaatgaaa | aattttggga | cccgaacttt | ccaagccata  1440 |
| actgttacta | aactgagtca | gaagtttacc | aaagttaatt | ttactgaaat | ccagaaacta  1500 |
| gtcctggatg | tggcccatgt | acatgagcac | tgttgcagag | gagatgtgct | ggattgtctg  1560 |
| caggatgggg | aaaaaatcat | gtcctacata | tgttctcaac | aagacactct | gtcaaacaaa  1620 |
| ataacagaat | gctgcaaaact | gaccacgctg | gaacgtggtc | aatgtataat | tcatgcagaa  1680 |
| aatgatgaaa | aacctgaagg | tctatctcca | aatctaaaca | ggttttagg  | agatagagat  1740 |
| tttaaccaat | tttcttcagg | ggaaaaaaat | atcttcttgg | caagttttgt | tcatgaatat  1800 |
| tcaagaagac | atcctcagct | tgctgtctca | gtaattctaa | gagttgctaa | aggataccag  1860 |
| gagttattgg | agaagtgttt | ccagactgaa | aaccctcttg | aatgccaaga | taaaggagaa  1920 |
| gaagaattac | agaaatacat | ccaggagagc | caagcattgg | caaagcgaag | ctgcggcctc  1980 |
| ttccagaaac | taggagaata | ttacttacaa | aatgcgtttc | tcgttgctta | cacaaagaaa  2040 |
| gccccccagc | tgacctcgtc | ggagctgatg | gccatcacca | gaaaaatggc | agccacagca  2100 |

```
gccacttgtt gccaactcag tgaggacaaa ctattggcct gtggcgaggg agcggctgac    2160
attattatcg acacttatg tatcagacat gaaatgactc cagtaaaccc tggtgttggc    2220
cagtgctgca cttcttcata tgccaacagg aggccatgct tcagcagctt ggtggtggat    2280
gaaacatatg tccctcctgc attctctgat gacaagttca ttttccataa ggatctgtgc    2340
caagctcagg gtgtagcgct gcaaacgatg aagcaagagt ttctcattaa ccttgtgaag    2400
caaaagccac aaataacaga ggaacaactt gaggctgtca ttgcagattt ctcaggcctg    2460
ttggagaaat gctgccaagg ccaggaacag gaagtctgct ttgctgaaga gggacaaaaa    2520
ctgatttcaa aaactcgtgc tgctttggga gtttaa                              2556
```

<210> SEQ ID NO 2
<211> LENGTH: 590
<212> TYPE: PRT
<213> ORGANISM: Homo sapiens

<400> SEQUENCE: 2

```
Thr Leu His Arg Asn Glu Tyr Gly Ile Ala Ser Ile Leu Asp Ser Tyr
1               5                   10                  15

Gln Cys Thr Ala Glu Ile Ser Leu Ala Asp Leu Ala Thr Ile Phe Phe
            20                  25                  30

Ala Gln Phe Val Gln Glu Ala Thr Tyr Lys Glu Val Ser Lys Met Val
        35                  40                  45

Lys Asp Ala Leu Thr Ala Ile Glu Lys Pro Thr Gly Asp Glu Gln Ser
    50                  55                  60

Ser Gly Cys Leu Glu Asn Gln Leu Pro Ala Phe Leu Glu Glu Leu Cys
65                  70                  75                  80

His Glu Lys Glu Ile Leu Glu Lys Tyr Gly His Ser Asp Cys Cys Ser
                85                  90                  95

Gln Ser Glu Glu Gly Arg His Asn Cys Phe Leu Ala His Lys Lys Pro
            100                 105                 110

Thr Pro Ala Ser Ile Pro Leu Phe Gln Val Pro Glu Pro Val Thr Ser
        115                 120                 125

Cys Glu Ala Tyr Glu Glu Asp Arg Glu Thr Phe Met Asn Lys Phe Ile
    130                 135                 140

Tyr Glu Ile Ala Arg Arg His Pro Phe Leu Tyr Ala Pro Thr Ile Leu
145                 150                 155                 160

Leu Trp Ala Ala Arg Tyr Asp Lys Ile Ile Pro Ser Cys Cys Lys Ala
                165                 170                 175

Glu Asn Ala Val Glu Cys Phe Gln Thr Lys Ala Ala Thr Val Thr Lys
            180                 185                 190

Glu Leu Arg Glu Ser Ser Leu Leu Asn Gln His Ala Cys Ala Val Met
        195                 200                 205

Lys Asn Phe Gly Thr Arg Thr Phe Gln Ala Ile Thr Val Thr Lys Leu
    210                 215                 220

Ser Gln Lys Phe Thr Lys Val Asn Phe Thr Glu Ile Gln Lys Leu Val
225                 230                 235                 240

Leu Asp Val Ala His Val His Glu His Cys Cys Arg Gly Asp Val Leu
                245                 250                 255

Asp Cys Leu Gln Asp Gly Glu Lys Ile Met Ser Tyr Ile Cys Ser Gln
            260                 265                 270

Gln Asp Thr Leu Ser Asn Lys Ile Thr Glu Cys Cys Lys Leu Thr Thr
        275                 280                 285
```

```
Leu Glu Arg Gly Gln Cys Ile Ile His Ala Glu Asn Asp Glu Lys Pro
        290                 295                 300
Glu Gly Leu Ser Pro Asn Leu Asn Arg Phe Leu Gly Asp Arg Asp Phe
305                 310                 315                 320
Asn Gln Phe Ser Ser Gly Glu Lys Asn Ile Phe Leu Ala Ser Phe Val
                325                 330                 335
His Glu Tyr Ser Arg Arg His Pro Gln Leu Ala Val Ser Val Ile Leu
            340                 345                 350
Arg Val Ala Lys Gly Tyr Gln Glu Leu Leu Glu Lys Cys Phe Gln Thr
        355                 360                 365
Glu Asn Pro Leu Glu Cys Gln Asp Lys Gly Glu Glu Leu Gln Lys
370                 375                 380
Tyr Ile Gln Glu Ser Gln Ala Leu Ala Lys Arg Ser Cys Gly Leu Phe
385                 390                 395                 400
Gln Lys Leu Gly Glu Tyr Tyr Leu Gln Asn Ala Phe Leu Val Ala Tyr
                405                 410                 415
Thr Lys Lys Ala Pro Gln Leu Thr Ser Ser Glu Leu Met Ala Ile Thr
            420                 425                 430
Arg Lys Met Ala Ala Thr Ala Ala Thr Cys Cys Gln Leu Ser Glu Asp
        435                 440                 445
Lys Leu Leu Ala Cys Gly Glu Gly Ala Ala Asp Ile Ile Ile Gly His
450                 455                 460
Leu Cys Ile Arg His Glu Met Thr Pro Val Asn Pro Gly Val Gly Gln
465                 470                 475                 480
Cys Cys Thr Ser Ser Tyr Ala Asn Arg Arg Pro Cys Phe Ser Ser Leu
                485                 490                 495
Val Val Asp Glu Thr Tyr Val Pro Pro Ala Phe Ser Asp Asp Lys Phe
            500                 505                 510
Ile Phe His Lys Asp Leu Cys Gln Ala Gln Gly Val Ala Leu Gln Thr
        515                 520                 525
Met Lys Gln Glu Phe Leu Ile Asn Leu Val Lys Gln Lys Pro Gln Ile
530                 535                 540
Thr Glu Glu Gln Leu Glu Ala Val Ile Ala Asp Phe Ser Gly Leu Leu
545                 550                 555                 560
Glu Lys Cys Cys Gln Gly Gln Glu Gln Glu Val Cys Phe Ala Glu Glu
                565                 570                 575
Gly Gln Lys Leu Ile Ser Lys Thr Arg Ala Ala Leu Gly Val
            580                 585                 590

<210> SEQ ID NO 3
<211> LENGTH: 30
<212> TYPE: DNA
<213> ORGANISM: artificial
<220> FEATURE:
<223> OTHER INFORMATION: chemically synthesized

<400> SEQUENCE: 3
cttaatcgat atgacactgc atagaaaatg                                      30

<210> SEQ ID NO 4
<211> LENGTH: 22
<212> TYPE: DNA
<213> ORGANISM: artificial sequence
<220> FEATURE:
<223> OTHER INFORMATION: chemically synthesized

<400> SEQUENCE: 4
```

```
cttccaagct actcccaagc ag                                        22

<210> SEQ ID NO 5
<211> LENGTH: 26
<212> TYPE: DNA
<213> ORGANISM: artificial sequence
<220> FEATURE:
<223> OTHER INFORMATION: chemically synthesized

<400> SEQUENCE: 5
caacctcgag ttaaaactcc caaagc                                    26

<210> SEQ ID NO 6
<211> LENGTH: 19
<212> TYPE: DNA
<213> ORGANISM: artificial sequence
<220> FEATURE:
<223> OTHER INFORMATION: chemically synthesized

<400> SEQUENCE: 6
ccaacccatg gctaagaga                                            19

<210> SEQ ID NO 7
<211> LENGTH: 23
<212> TYPE: DNA
<213> ORGANISM: artificial sequence
<220> FEATURE:
<223> OTHER INFORMATION: chemically synthesized

<400> SEQUENCE: 7
gaagtaattt aaactcccaa agc                                       23
```